United States Patent
de Maeyer et al.

(10) Patent No.: US 10,973,820 B2
(45) Date of Patent: Apr. 13, 2021

(54) COMPOUNDS FOR TREATMENT OF DISEASES RELATED TO DUX4 EXPRESSION

(71) Applicant: Facio Intellectual Property B.V., Leiden (NL)

(72) Inventors: Joris de Maeyer, Mechelen (BE); Marcus Geese, Göttingen (DE); Martin Schneider, Göttingen (DE); Sebastian Monecke, Göttingen (DE); Alexander Kaever, Göttingen (DE); Monika Ermann, Abingdon (GB); Timothy Robin James, Abingdon (GB)

(73) Assignee: Facio Intellectual Property B.V., Leiden (NL)

( * ) Notice: Subject to any disclaimer, the term of this patent is extended or adjusted under 35 U.S.C. 154(b) by 0 days.

(21) Appl. No.: 16/217,184

(22) Filed: Dec. 12, 2018

(65) Prior Publication Data

US 2019/0175596 A1 Jun. 13, 2019

(30) Foreign Application Priority Data

Dec. 13, 2017 (EP) .................................. 17207162

(51) Int. Cl.
| | |
|---|---|
| *A61K 31/506* | (2006.01) |
| *A61K 31/5025* | (2006.01) |
| *A61K 31/4355* | (2006.01) |
| *A61P 21/00* | (2006.01) |
| *A61K 31/4439* | (2006.01) |
| *A61K 31/5377* | (2006.01) |
| *A61K 31/437* | (2006.01) |

(52) U.S. Cl.
CPC .......... *A61K 31/506* (2013.01); *A61K 31/437* (2013.01); *A61K 31/4355* (2013.01); *A61K 31/4439* (2013.01); *A61K 31/5025* (2013.01); *A61K 31/5377* (2013.01); *A61P 21/00* (2018.01)

(58) Field of Classification Search
CPC .................................................... A61K 31/506
See application file for complete search history.

(56) References Cited

U.S. PATENT DOCUMENTS

| | | |
|---|---|---|
| 2005/0131012 A1 | 6/2005 | Metz |
| 2015/0087636 A1 | 3/2015 | Sverdrup |

FOREIGN PATENT DOCUMENTS

| | | | |
|---|---|---|---|
| EP | 2949651 A1 | * 12/2015 | ........... A61K 31/428 |
| EP | 2949651 A1 | 12/2015 | |
| WO | WO2009/016286 A2 | 2/2009 | |
| WO | WO2012/085721 A1 | 6/2012 | |
| WO | WO2015/114638 A1 | 8/2015 | |
| WO | WO2015119579 A1 | 8/2015 | |
| WO | WO2015195880 A1 | 12/2015 | |

OTHER PUBLICATIONS

Hoffman, Muscular Dystrophies, Principles of Molecular Medicine pp. 859-863, 1888.*
Brockschmidt, et al. "Anti-apoptotic and growth-stimulatory functions of CK1 delta and epsilon in ductal adenocarcinoma of the pancreas are inhibited by IC261 in vitro and in vivo." Gut 57.6 (2008): 799-806.
Lemmers, et al. "A unifying genetic model for facioscapulohumeral muscular dystrophy." Science (2010): 1189044.
Snider, et al. "Facioscapulohumeral dystrophy: incomplete suppression of a retrotransposed gene." PLoS genetics 6.10 (2010): e1001181.
Tawil et al "Facioscapulohumeral dystrophy: the path to consensus on pathophysiology." Skeletal muscle 4.1 (2014): 12.
Van Den Boogaard., et al. "Mutations in DNMT3B modify epigenetic repression of the D4Z4 repeat and the penetrance of facioscapulohumeral dystrophy." The American Journal of Human Genetics 98.5 (2016): 1020-1029.
Yao, et al. "DUX4-induced gene expression is the major molecular signature in FSHD skeletal muscle." Human molecular genetics 23.20 (2014): 5342-5352.
Campbell, et al. "BET bromodomain inhibitors and agonists of the beta-2 adrenergic receptor identified in screens for compounds that inhibit DUX4 expression in FSHD muscle cells." Skeletal muscle 7.1 (2017): 16.
Yasuda et al. "Recurrent DUX4 fusions in B cell acute lymphoblastic leukemia of adolescents and young adults." Nature genetics 48.5 (2016): 569.
Oyama, et al. "Generation of novel patient-derived CIC-DUX4 sarcoma xenografts and cell lines." Scientific reports 7.1 (2017): 4712.
Bergerat, et al. "Primary CIC-DUX4 round cell sarcoma of the kidney: A treatment-refractory tumor with poor outcome." Pathology-Research and Practice 213.2 (2017): 154-160.

* cited by examiner

*Primary Examiner* — Svetlana M Ivanova
(74) *Attorney, Agent, or Firm* — NLO; Catherine Shulz; Tamara Stegmann

(57) ABSTRACT

The present invention relates to compounds for the treatment of diseases related to DUX4 expression, such as muscular dystrophies, wherein the disease is facioscapulohumeral muscular dystrophy (FSHD). It also relates to use of such compounds, or to methods of use of such compounds.

Figure 1:
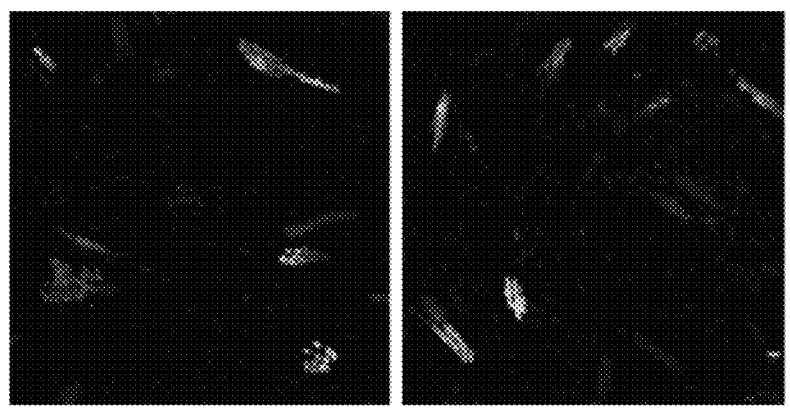
Figure 1:
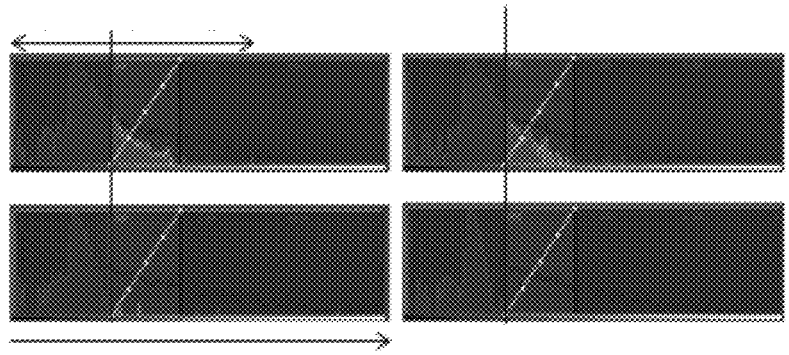
Figure 1:
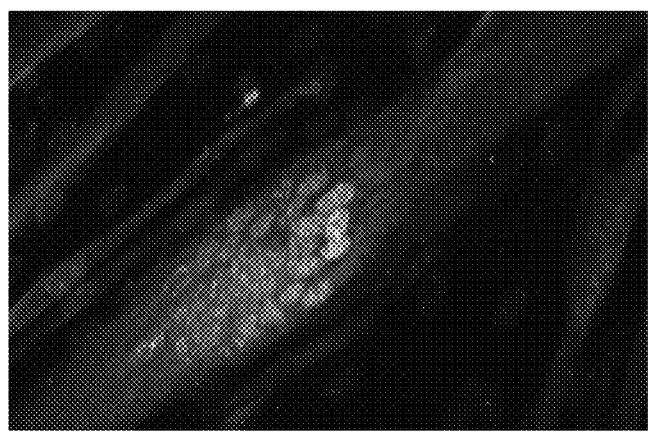
Figure 1:

12 Claims, 13 Drawing Sheets
Specification includes a Sequence Listing.

A

B

A

B

A

B

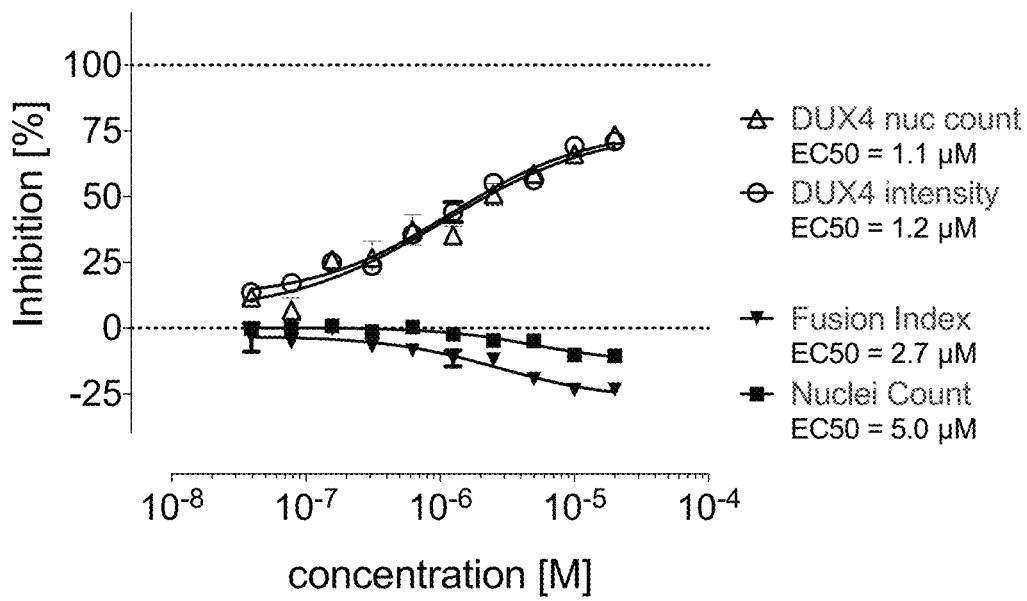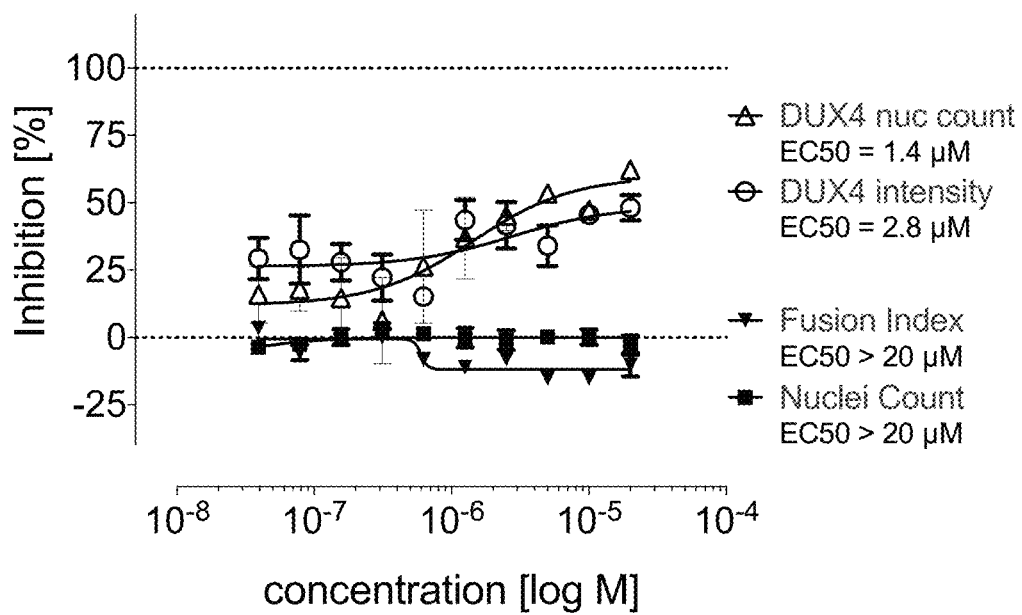

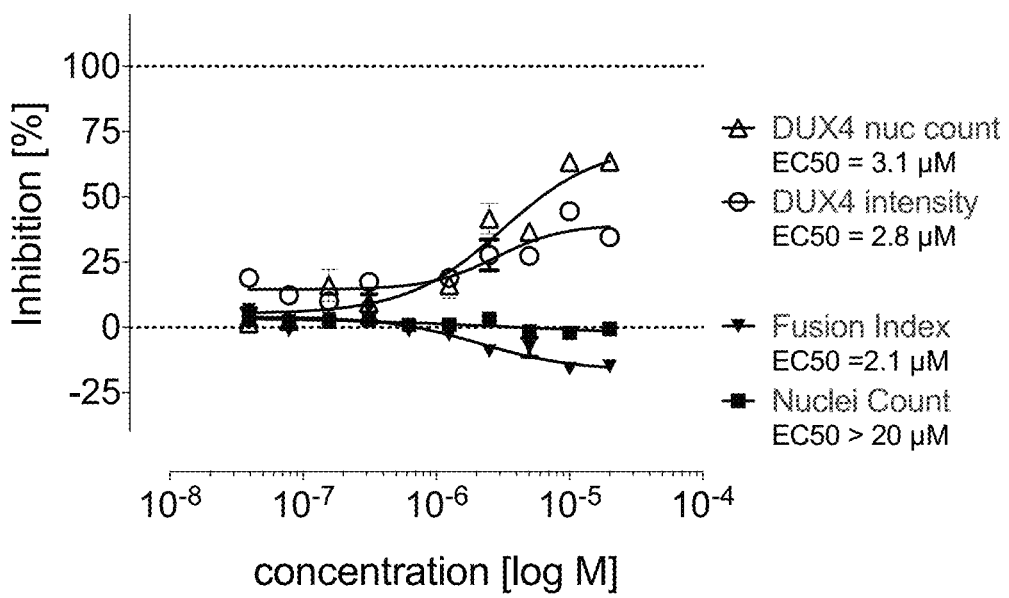
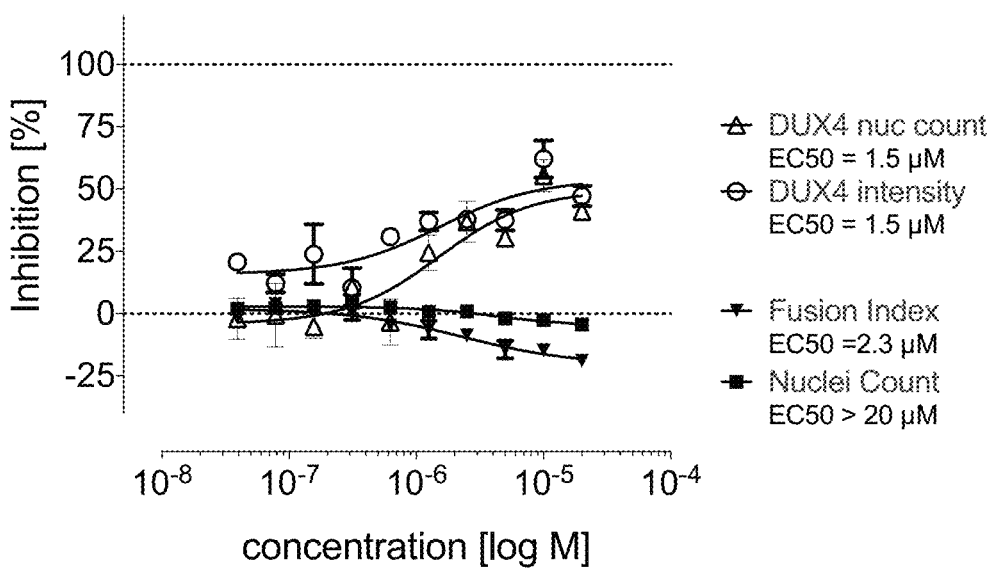

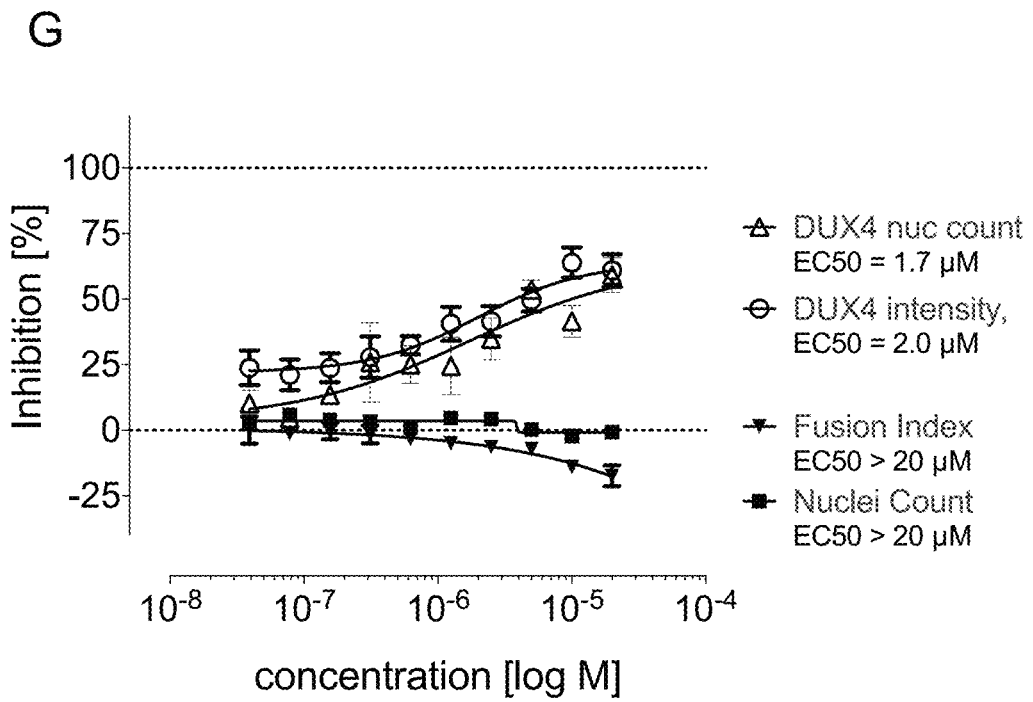
Fig. 6
A
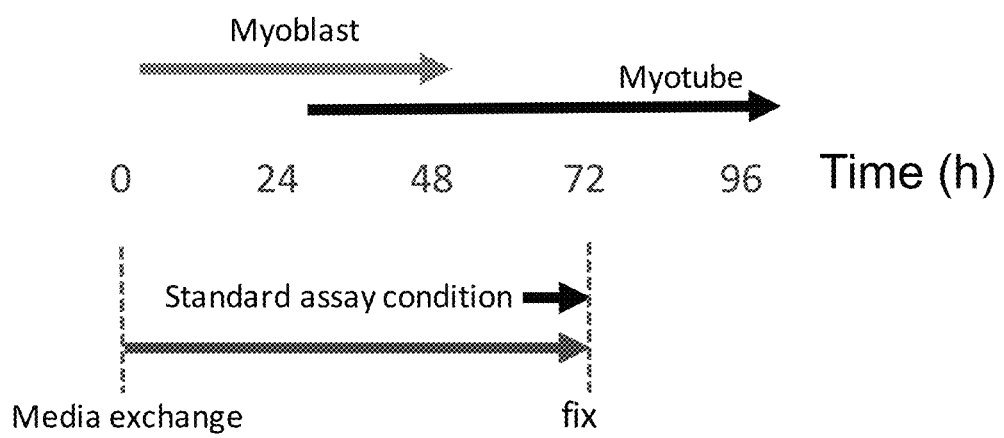

B
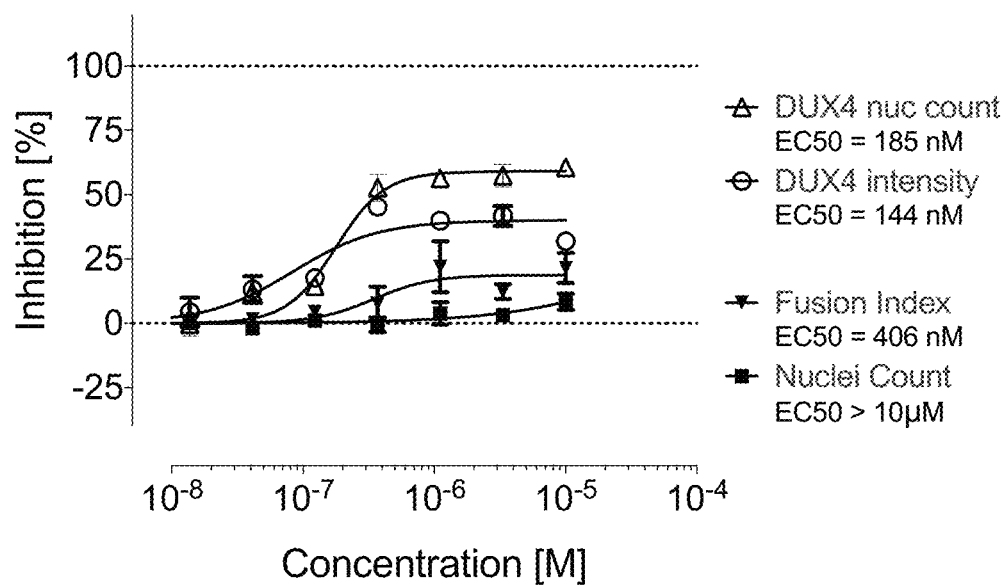
C
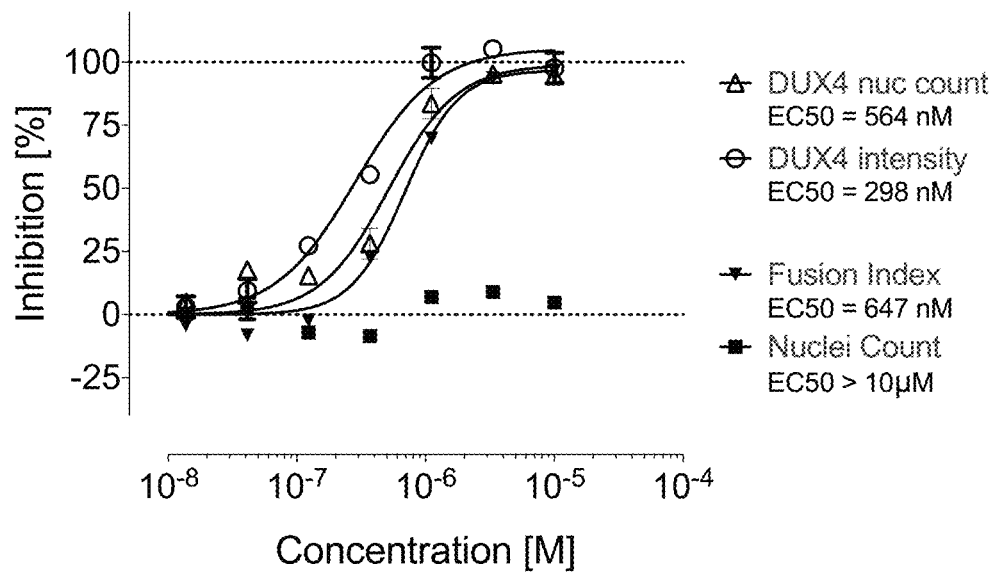

D
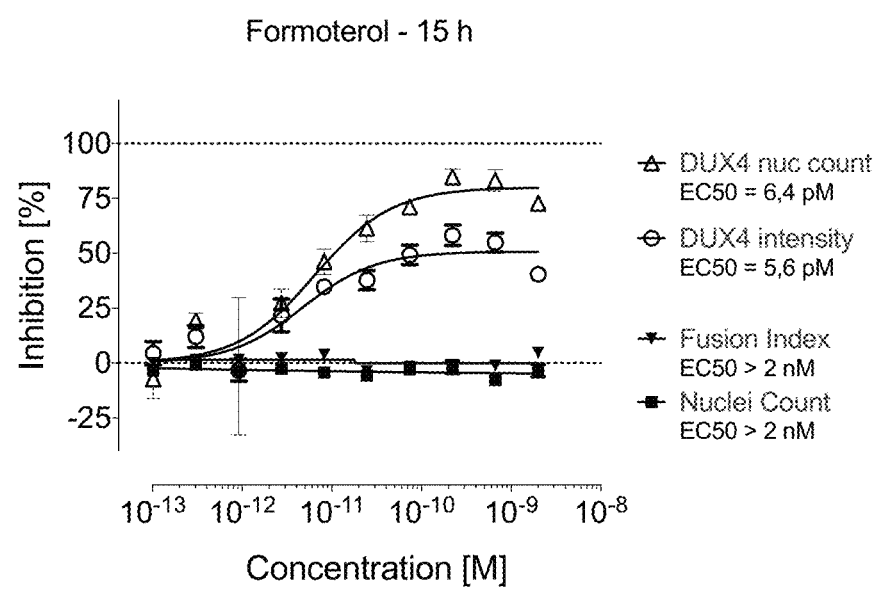
E
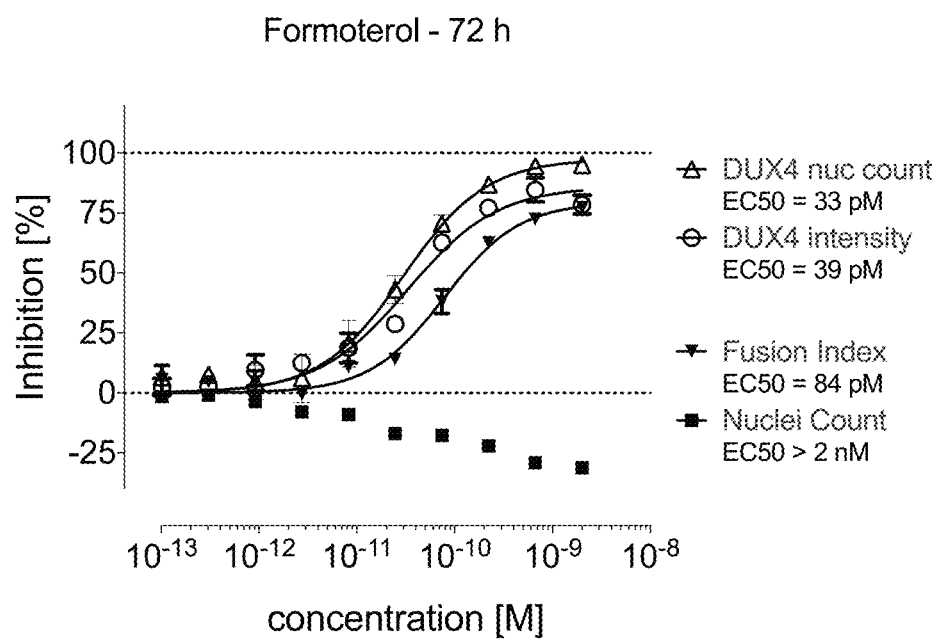

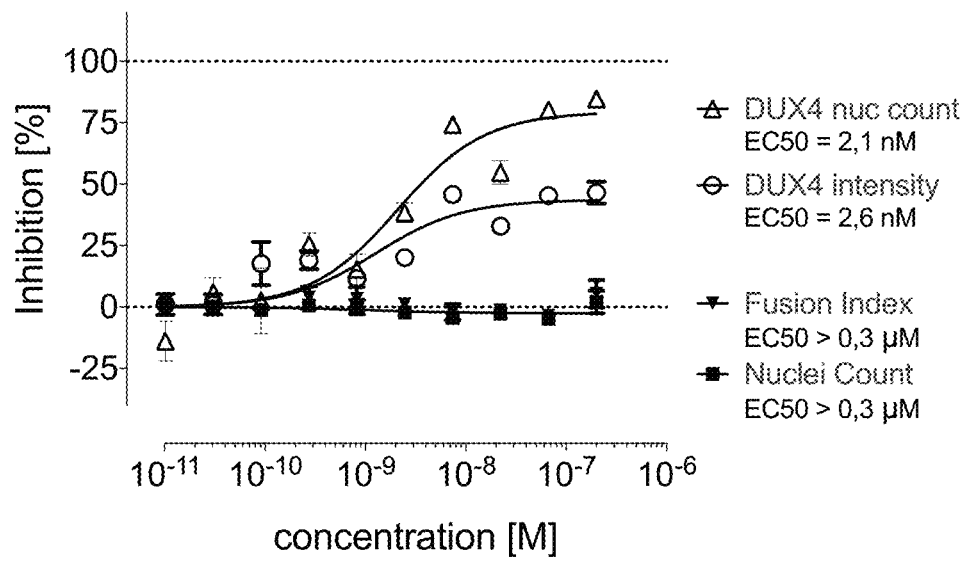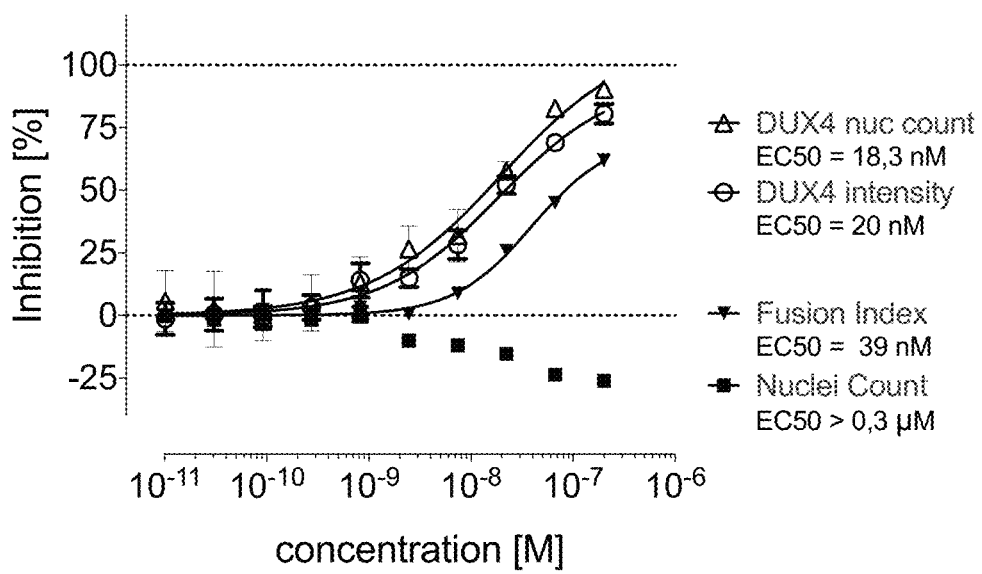

H
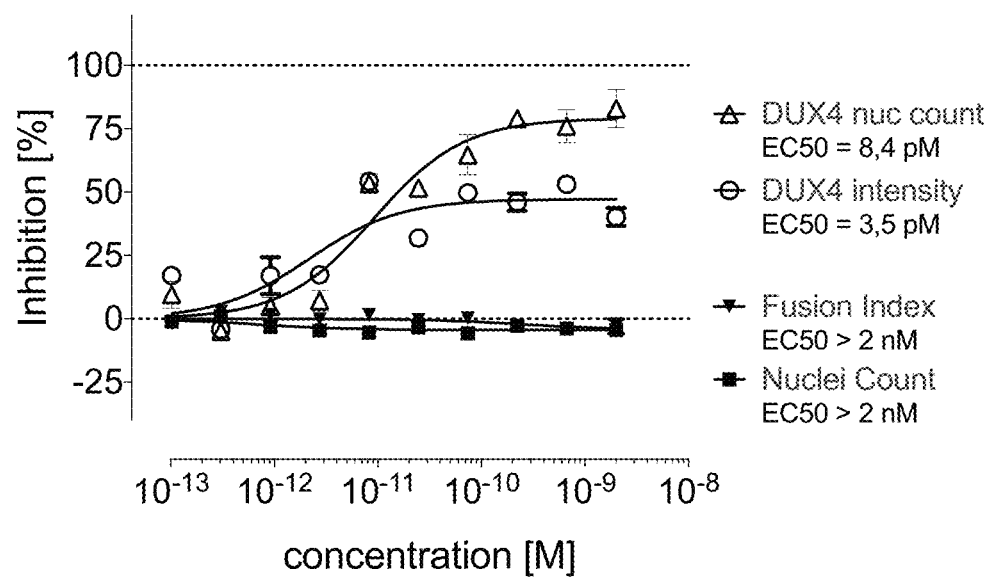
I
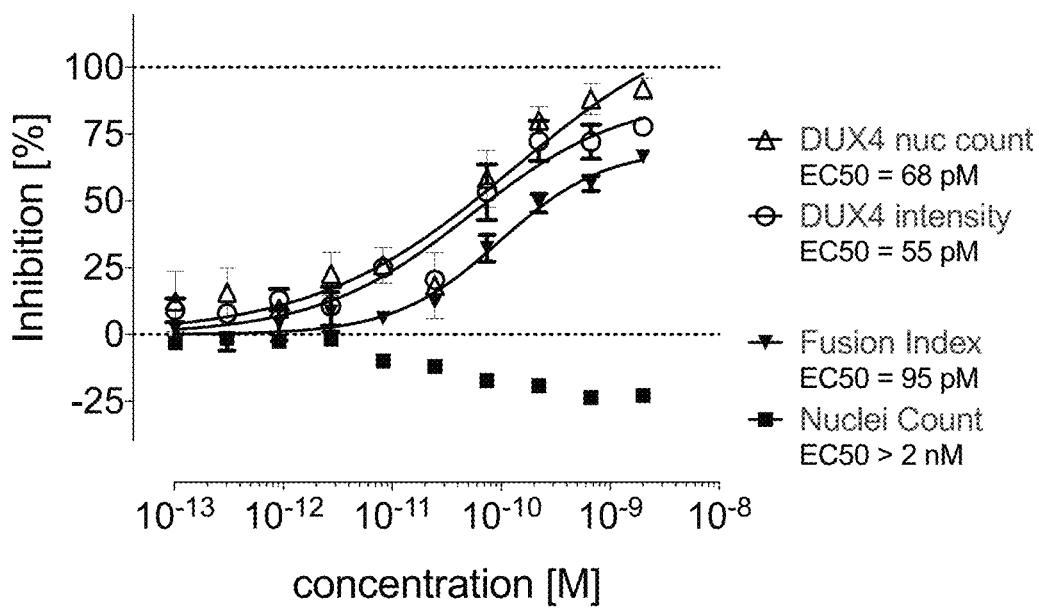

J
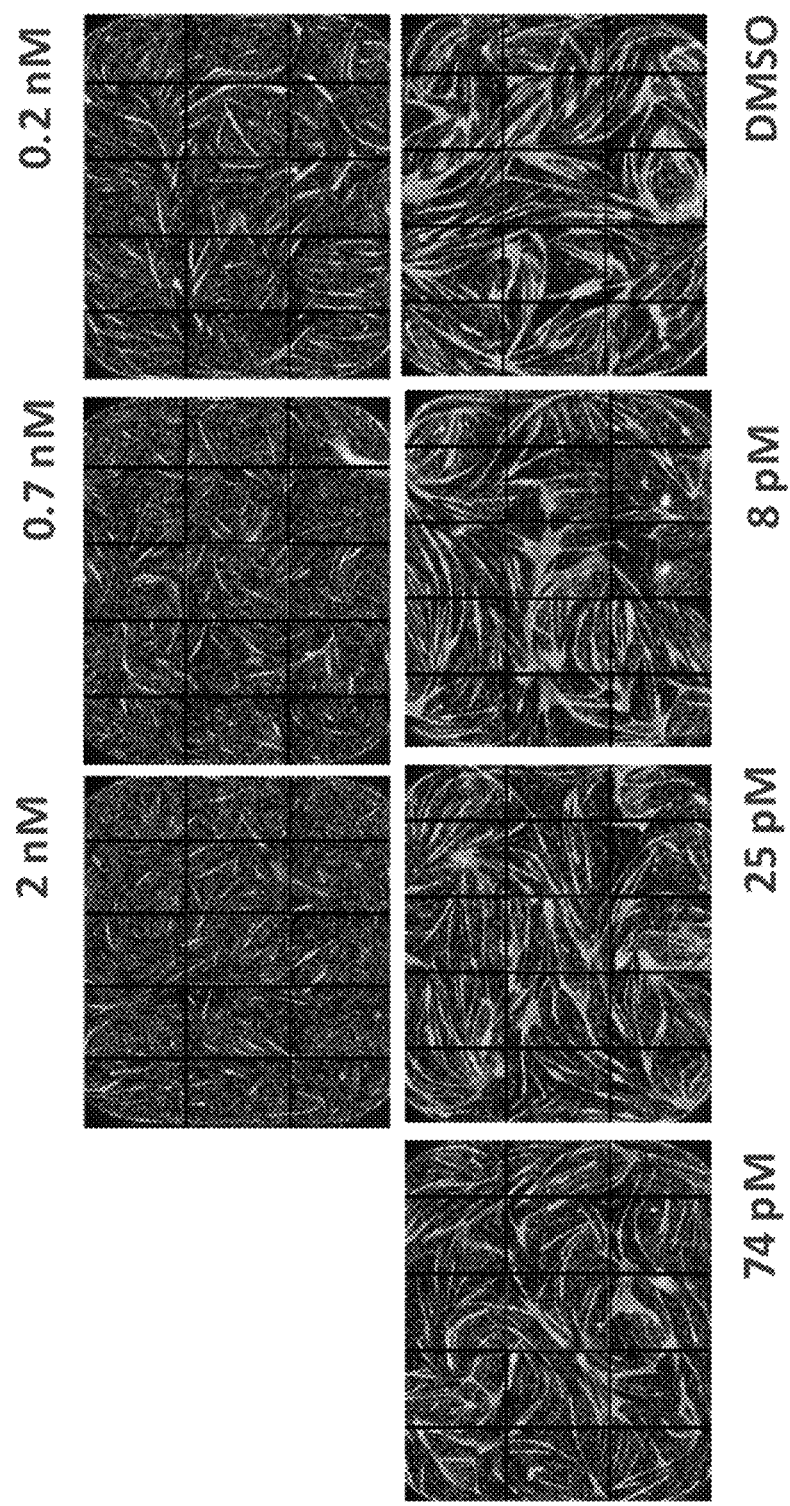

K
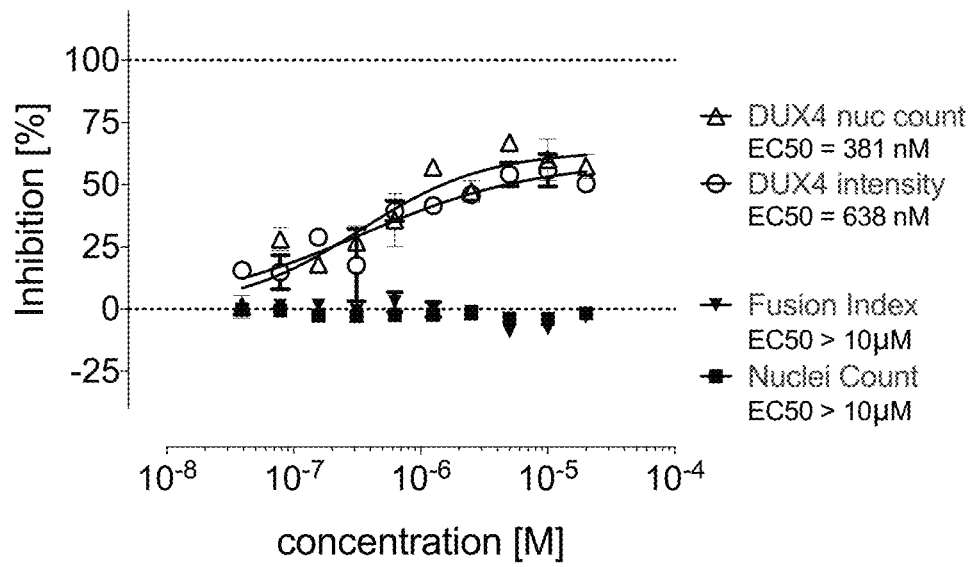
L
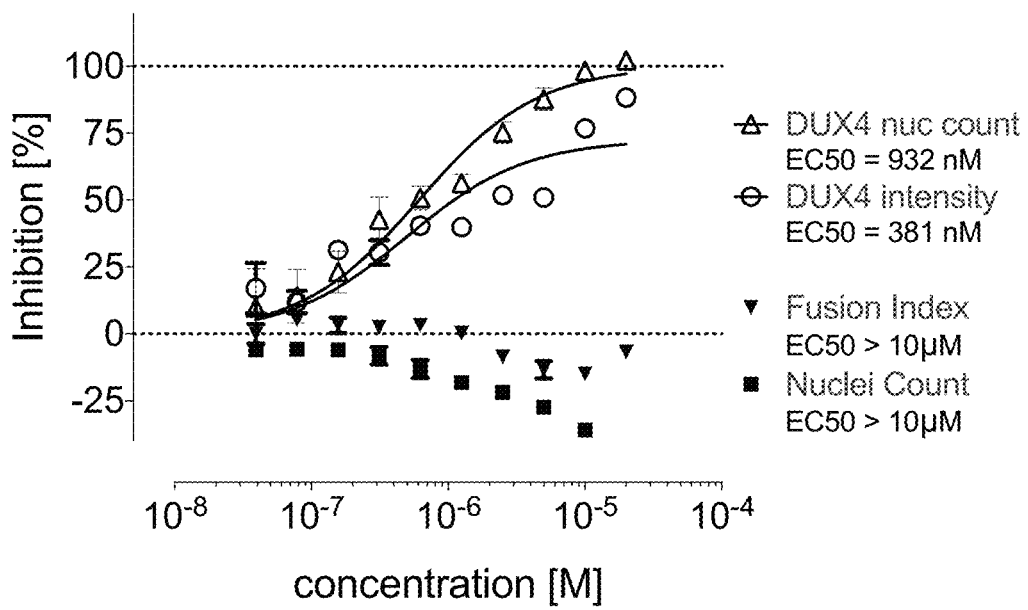

```
                      SEQUENCE LISTING

<160> NUMBER OF SEQ ID NOS: 15

<210> SEQ ID NO 1
<211> LENGTH: 16
<212> TYPE: DNA
<213> ORGANISM: Artificial Sequence
<220> FEATURE:
<223> OTHER INFORMATION: hDUX4 forward Primer for qPCR

<400> SEQUENCE: 1
cccggctgac gtgcaa                                                   16

<210> SEQ ID NO 2
<211> LENGTH: 22
<212> TYPE: DNA
<213> ORGANISM: Artificial Sequence
<220> FEATURE:
<223> OTHER INFORMATION: hDUX4 reverse Primer for qPCR

<400> SEQUENCE: 2
agccagaatt tcacggaaga ac                                            22

<210> SEQ ID NO 3
<211> LENGTH: 22
<212> TYPE: DNA
<213> ORGANISM: Artificial Sequence
<220> FEATURE:
<223> OTHER INFORMATION: hDUX4 probe Primer for qPCR

<400> SEQUENCE: 3
agctcgctgg cctctctgtg cc                                            22

<210> SEQ ID NO 4
<211> LENGTH: 21
<212> TYPE: DNA
<213> ORGANISM: Artificial Sequence
<220> FEATURE:
<223> OTHER INFORMATION: hGUSB forward Primer for qPCR

<400> SEQUENCE: 4
ttccctccag cttcaatgac a                                             21

<210> SEQ ID NO 5
<211> LENGTH: 17
<212> TYPE: DNA
<213> ORGANISM: Artificial Sequence
<220> FEATURE:
<223> OTHER INFORMATION: hGUSB reverse Primer for qPCR
```

<400> SEQUENCE: 5
ccacacccag ccgacaa					17

<210> SEQ ID NO 6
<211> LENGTH: 19
<212> TYPE: DNA
<213> ORGANISM: Artificial Sequence
<220> FEATURE:
<223> OTHER INFORMATION: hGUSB probe Primer for qPCR

<400> SEQUENCE: 6
aggactggcg tctgcggca					19

<210> SEQ ID NO 7
<211> LENGTH: 20
<212> TYPE: DNA
<213> ORGANISM: Artificial Sequence
<220> FEATURE:
<223> OTHER INFORMATION: hRPL27 forward Primer for qPCR

<400> SEQUENCE: 7
tgtcctggct ggacgctact					20

<210> SEQ ID NO 8
<211> LENGTH: 23
<212> TYPE: DNA
<213> ORGANISM: Artificial Sequence
<220> FEATURE:
<223> OTHER INFORMATION: hRPL27 reverse Primer for qPCR

<400> SEQUENCE: 8
gaggtgccat catcaatgtt ctt				23

<210> SEQ ID NO 9
<211> LENGTH: 21
<212> TYPE: DNA
<213> ORGANISM: Artificial Sequence
<220> FEATURE:
<223> OTHER INFORMATION: hRPL27 probe Primer for qPCR

<400> SEQUENCE: 9
cggacgcaaa gctgtcatcg t					21

<210> SEQ ID NO 10
<211> LENGTH: 22
<212> TYPE: DNA
<213> ORGANISM: Artificial Sequence
<220> FEATURE:
<223> OTHER INFORMATION: hZSCAN4 forward Primer for qPCR

<400> SEQUENCE: 10
aggcaggaat tgcaaagact tt				22

<210> SEQ ID NO 11
<211> LENGTH: 23
<212> TYPE: DNA
<213> ORGANISM: Artificial Sequence
<220> FEATURE:
<223> OTHER INFORMATION: hZSCAN4 reverse Primer for qPCR

<400> SEQUENCE: 11
aatttcatcc ttgctgtgct ttt				23

<210> SEQ ID NO 12

```
<211> LENGTH: 28
<212> TYPE: DNA
<213> ORGANISM: Artificial Sequence
<220> FEATURE:
<223> OTHER INFORMATION: hZSCAN4 probe Primer for qPCR

<400> SEQUENCE: 12
taggatcttt cactcatggc tgcaacca                                          28

<210> SEQ ID NO 13
<211> LENGTH: 19
<212> TYPE: DNA
<213> ORGANISM: Artificial Sequence
<220> FEATURE:
<223> OTHER INFORMATION: hMYOG forward Primer for qPCR

<400> SEQUENCE: 13
gctcacggct gaccctaca                                                    19

<210> SEQ ID NO 14
<211> LENGTH: 21
<212> TYPE: DNA
<213> ORGANISM: Artificial Sequence
<220> FEATURE:
<223> OTHER INFORMATION: hMYOG reverse Primer for qPCR

<400> SEQUENCE: 14
cactgtgatg ctgtccacga t                                                 21

<210> SEQ ID NO 15
<211> LENGTH: 24
<212> TYPE: DNA
<213> ORGANISM: Artificial Sequence
<220> FEATURE:
<223> OTHER INFORMATION: hMYOG probe Primer for qPCR

<400> SEQUENCE: 15
cccacaacct gcactccctc acct                                              24
```

COMPOUNDS FOR TREATMENT OF DISEASES RELATED TO DUX4 EXPRESSION

FIELD OF THE INVENTION

The present invention relates to compounds for the treatment of diseases related to DUX4 expression, such as muscular dystrophies, wherein the disease is facioscapulohumeral muscular dystrophy (FSHD). It also relates to use of such compounds, or to methods of use of such compounds.

BACKGROUND ART

Serine/threonine kinases (EC 2.7.11.1) are a class of protein kinases that are promising drug targets for small molecule inhibitors. Due to their involvement in signaling pathways in eukaryotic cells, inhibition of serine/threonine kinases is likely to have relevance to the treatment of diseases such as cancer, diabetes, and a variety of inflammatory disorders.

Casein kinase 1 (CK1, also known as CSNK1) belongs to the serine/threonine kinase family. CK1 isoforms are involved in Wnt signaling, circadian rhythms, nucleo-cytoplasmic shuttling of transcription factors, DNA repair, and DNA transcription (Eide E J, Virshup D M (2001) doi: 10.1081/CBI-100103963). In mammals, the enzyme exists in seven isoforms: $\alpha$, $\beta$, $\gamma1$, $\gamma2$, $\gamma3$, $\delta$, and $\varepsilon$, all having a similar kinase domain. Through phosphorylation of different substrate proteins, these isoforms are able to activate, stabilize, inactivate, or destabilize the functions of these substrate proteins, thus regulating their functions. For example, a tumor suppressor factor p53 and an oncogene mdm2, which are both important proteins for controlling abnormal cell growth, are substrates of CK1.

Mammalian casein kinases such as casein kinase 1$\gamma$, casein kinase 1$\delta$, and casein kinase 1$\varepsilon$ are important regulators of various cellular growth and survival processes including Wnt signaling, circadian rhythms, and DNA repair. They have a kinase domain similar to those of other isoforms. However, their N-terminal and C-terminal domains are different from those of other isoforms. The C-terminal domain has a plurality of autophosphorylation sites, and is considered to be involved in regulation of autoenzyme activity. Phosphorylation of p53 by casein kinases such as casein kinase 1$\delta$ or casein kinase 1$\varepsilon$ leads to a change in the interaction between p53 and mdm2. It has also been known that casein kinase 1$\delta$ and casein kinase 1$\varepsilon$ are involved as a regulatory protein associated with the formation of a spindle as a central body during cell division, and that casein kinase 1$\delta$ and casein kinase 1$\varepsilon$ are involved in apoptosis mediated by TRAIL (tumor necrosis factor-related apoptosis inducing factor) and Fas. It has been further reported that inhibition of casein kinase 1$\delta$ or casein kinase 1$\varepsilon$ by a nonselective CK1 inhibitory compound IC261 reduces pancreatic tumor cell growth in vitro and in vivo (Brockschmidt et al., 2008, DOI: 10.1136/gut.2007.123695). Hence, CK1 inhibitors have been developed and investigated for various important phenotypic and therapeutic effects.

WO2011051858 discloses CK1 inhibitors (both $\delta$ and $\varepsilon$) useful in the treatment and/or prevention of diseases and disorders associated with the central nervous system. These inhibitors form a series of substituted imidazole compounds, more specifically a series of 4-aryl-5-heteroaryl-1-heterocycloalkyl-imidazoles and related analogs. Both their synthesis and $IC_{50}$ values for CK1 $\delta$ and $\varepsilon$ are reported, the latter of which generally fall in the nanomolar range. A closely related family of CK1 inhibitors is disclosed in WO2012085721.

WO2015119579 discloses a family that also features an azole core, namely a family of 2,4,5-tri-substituted azole compounds for use as CK1 inhibitors. The inhibitors are used for inducing or enhancing the differentiation of pluripotent stem cells into cardiomyocytes via CK1 inhibition. Synthetic pathways for obtaining the inhibitors are disclosed, and the inhibitors are shown to generally have $IC_{50}$ values in the nanomolar range as CK1 $\delta$ ands inhibitors.

EP2949651 discloses a family of derivatives of substituted benzothiazoles that act as CK1 inhibitors, and their use is coupled to the treatment and/or prevention of diseases mediated by CK1, especially inflammatory, neurological, psychiatric, neurodegenerative and/or ophthalmic diseases and certain regenerative processes. Methods of synthesis are provided, and the inhibitors were shown to have nanomolar inhibitory activity on CK1 $\delta$ and $\varepsilon$.

WO2009016286 discloses 6-cycloamino-3-(pyrid-4-yl) imidazo[1,2-b]pyridazine derivatives useful as protein kinase inhibitors, particularly as CK1$\delta$ ands inhibitors. Their synthesis is described in detail, and the capacity of the CK1 inhibitors to inhibit the phosphorylation of casein by casein kinases 1$\delta$ and $\varepsilon$ was evaluated according to the procedure described in US2005/0131012, revealing $IC_{50}$ values in the nanomolar range.

WO2015195880 discloses a family with a similar core, namely substituted bicyclic pyrazoles useful as protein kinase inhibitors. Synthetic strategies for obtaining the inhibitors are described, and the resulting CK1 inhibitors were shown to be effective on CK1 $\delta$ and $\varepsilon$. A particular relevance is indicated for the treatment of cancer.

Facioscapulohumeral muscular dystrophy (FSHD) is the most prevalent hereditary muscular dystrophy. Symptoms begin before the age of 20, with weakness and atrophy of the muscles around the eyes and mouth, shoulders, upper arms and lower legs. Later, weakness can spread to abdominal muscles and sometimes hip muscles with approximately 20% of patients eventually becoming wheelchair-bound. Patients currently rely on treatment of symptoms like pain and fatigue, involving the use of pain medication, cognitive therapy and physical exercise, sometimes supplemented with medical devices used to maintain the patient's mobility. Furthermore, increased scapular function may be obtained by surgical treatment of the scapula. At best, these interventions remain symptomatic in nature and do not affect disease progression, illustrating the need for a therapy that is able to modify disease progression.

Significant progress has been made in recent years in the understanding of the molecular basis of FSHD. This resulted in the identification and characterization of the fundamental genetic lesions causing FSHD, giving rise to a new pathogenesis model in which epigenetic de-repression of the Double Homeobox 4 (DUX4) retrogene in muscle cells triggers pathology by initiating a transcription deregulation cascade that causes muscle atrophy, inflammation, and oxidative stress, which are key features of the disease. DUX4 shares similarities with transcription factors and it is normally abundantly expressed in germ cells of human testes, while being epigenetically repressed in somatic tissues. There is the wide support for the pathogenesis model in which gain-of-function of the DUX4 gene in muscle cells underlies FSHD etiology (Lemmers et al., 2010, DOI: 10.1126/science.1189044; Sharma et al., 2016, DOI:

10.4172/2157-7412.1000303, Snider et al., 2010, DOI: 10.1371/journal.pgen.1001181; Tawil et al., 2014, DOI: 10.1186/2044-5040-4-12).

FSHD is sometimes divided in two subtypes, namely FSHD1 and FSHD2. FSHD1 is associated with large deletions within a DNA tandem array (D4Z4) that is located in the subtelomeric region of chromosome 4q35. Each of the D4Z4 repeats contains a copy of the DUX4 gene, which is normally silenced in somatic tissues of healthy individuals. Healthy, genetically unaffected individuals are defined as having between 10 and 100 D4Z4 repeat units on both 4q chromosome arms, whereas individuals with FSHD1 have between 1 and 10 D4Z4 repeat units on one 4q chromosome arm. The deletions of D4Z4 repeats that characterize FSHD remove a substantial portion of regulatory chromatin from this region, including several hundreds of histones and a significant amount of CpG-rich DNA. These elements are essential in the establishment of DNA methylation and heterochromatin and their loss significantly alters the epigenetic status of the D4Z4 array. The contraction of D4Z4 is by itself not pathogenic. Only when the contraction of D4Z4 occurs on a disease-permissive 4qA allele, containing a polymorphism that could affect the polyadenylation of the distal DUX4 transcript, the altered epigenetic context is associated with alternative splicing and increased expression of DUX4 in skeletal muscles of FSHD1 patients. In the much rarer form FSHD2, the cause is a mutated form of an epigenetic factor such as SMCHD1 or DNMT3B. In this form as well, the D4Z4 region is hypomethylated and muscle cells are characterized by a de-repressed DUX4 protein. Both forms of FSHD converge on undue DUX4 expression. It has therefore been suggested that FSHD1 and FSHD2 are on a continuum, rather than being separate (Van den Boogaard et al., 2016, DOI: 10.1016/j.ajhg.2016.03.013).

DUX4 acts as a transcription factor whose expression initiates a transcription cascade resulting in progressive muscle cell dysfunction and death, and ultimately to overt pathology (Kowaljow et al., 2007, DOI: 10.1016/j.nmd.2007.04.002; Vanderplanck et al., 2011, doi: 10.1371/journal.pone.0026820; Geng et al., 2012, DOI: 10.1016/j.devcel.2011.11.013; Yao et al., 2014, DOI: 10.1093/hmg/ddu251; Wallace et al., 2011, DOI: 10.1002/ana.22275). In healthy individuals, DUX4 is expressed in the germline, but is epigenetically silenced in somatic tissues. In FSHD patients, burst-like DUX4 expression in only a small fraction of myofibers causes myocyte death ultimately leading to muscle weakness and wasting (Lemmers et al., 2010). In the simplest terms, DUX4-overexpression is a primary pathogenic insult underlying FSHD, and its repression is a promising therapeutic approach for FSHD. In support of this, short repeat sizes are generally associated with a severe FSHD phenotype. Moderate repeat contractions have a milder and more variable clinical severity. A very rare subtype of FSHD, named FSHD2, is characterized by a moderate repeat contraction (>10 repeats remaining), and is associated with mutations in the SMCHD1 gene or in the DNMT3B gene. Also in FSHD2, the D4Z4 region is hypomethylated and muscle cells are characterized by a de-repressed DUX4 protein. Patients with less than 10 D4Z4 repeat units that also have a mutation in SMCHD1 have a very severe clinical phenotype, illustrating that a combination of repeat size and activity of epigenetic modifiers, both contributing to derepression of DUX4, determines the eventual disease severity in FSHD.

Campbell et al. (2017, DOI 10.1186/s13395-017-0134-x) screened a selection of chemical compounds with known epigenetic activities as well as the Pharmakon 1600 library composed of compounds that have reached clinical testing to identify molecules that decrease DUX4 expression as monitored by the expression levels of DUX4 target gene mRNAs in immortalized FSHD skeletal muscle cell cultures. They identified several classes of molecules that include inhibitors of the bromodomain and extra-terminal (BET) family of proteins and agonists of the beta-2 adrenergic receptor. Their studies suggest that compounds from these two classes suppress the expression of DUX4 by blocking the activity of bromodomain-containing protein 4 (BRD4) or by increasing cyclic adenosine monophosphate (cAMP) levels, respectively.

Because of its causative role in FSHD, suppressing DUX4 is a primary therapeutic approach for halting disease progression. This approach could also be useful for treating other diseases, such as cancers including acute lymphoblastic leukemia (Yasuda et al., 2016, doi: 10.1038/ng.3535) and sarcomas (Oyama et al., 2017 DOI: 10.1038/s41598-017-04967-0; Bergerat et al., 2017, DOI: 10.1016/j.prp.2016.11.015), etc. However, the mechanisms behind DUX4 expression are poorly understood and corresponding drug targets are poorly defined. As a result, there is no treatment for FSHD at present, and there is a need for compounds and compositions that can be used to suppress DUX4 expression.

SUMMARY OF THE INVENTION

In a first aspect, the invention provides a casein kinase 1 inhibitor for use in the treatment of a disease or condition associated with DUX4 expression, wherein the casein kinase 1 inhibitor reduces DUX4 expression. Preferably, the disease or condition associated with DUX4 expression is a muscular dystrophy or cancer, preferably wherein said disease or condition associated with DUX4 expression is a muscular dystrophy, most preferably facioscapulohumeral muscular dystrophy (FSHD). Preferably, the casein kinase 1 inhibitor is characterized in that it is administered to a subject 4, 3, 2, or 1 times per day or less, preferably 1 time per day. Preferably, the casein kinase 1 inhibitor inhibits at least, and optionally is specific for, casein kinase 1δ. Preferably, the CK1 inhibitor is characterized in that it is administered to a subject in an amount ranging from 0.1 to 400 mg/day, preferably from 0.25 to 150 mg/day. Preferably, the casein kinase 1 inhibitor is characterized in that it is administered orally, sublingually, intravascularly, intravenously, subcutaneously, or transdermally, preferably orally. Preferably, DUX4 expression is reduced by at least 30%, 40%, 60%, 80%, or more. Preferably, the casein kinase 1 inhibitor reduces DUX4 expression in muscle cells, immune cells, or cancer cells. Preferably, the reduction of DUX4 expression is determined using PCR or immunostaining. Preferably, the casein kinase 1 inhibitor is from the class comprising an azole core. Preferably, the casein kinase 1 inhibitor is selected from the group consisting of compounds A, B, C, D, E, F, G, H, I, J, K, L, M, N, O, PF-670462, and PF-5006739.

In a second aspect the invention provides a composition comprising at least one casein kinase 1 inhibitor as defined in the first embodiment, and a pharmaceutically acceptable excipient, for use as defined in the first embodiment. Preferably, the composition for use is formulated for oral, sublingual, parenteral, intravascular, intravenous, subcutaneous, or transdermal administration, preferably for oral administration.

In a third aspect, the invention provides an in vivo, in vitro, or ex vivo method for reducing DUX4 expression, the method comprising the step of contacting a cell with a casein kinase 1 inhibitor as defined in the first aspect, or with a composition as defined in the second aspect. In a fourth aspect, the invention provides a method for reducing DUX4 expression in a subject in need thereof, the method comprising the step of administering an effective amount of a casein kinase 1 inhibitor as defined in the first aspect, or a composition as defined in the second aspect.

DESCRIPTION OF EMBODIMENTS

Following the central role of DUX4 in the consensus disease hypothesis for FSHD, a therapeutic approach with a disease-modifying potential is expected to rely on the inhibition of DUX4. The inventors have surprisingly identified Caseine kinase 1 (CK1) as a novel drug target to achieve DUX4 repression in muscle cells. This invention has been made using primary FSHD patient-derived muscle cells. Because of the primate-specificity of the FSHD locus and questionable relevance of recombinant, immortalized, or tumorigenic cell or animal models to study endogenous DUX4 regulatory mechanisms, primary patient-derived muscle cells are the most relevant disease model available. Assays based on immortalized cells bear the risk of altered epigenomes, thereby limiting their relevance in studying the endogenous regulation of DUX4 expression. Particularly the subtelomeric location of D4Z4 and the importance of the D4Z4 epigenome in the stability of DUX4 repression (Stadler et al., 2013, DOI: 10.1038/nsmb.2571) underscore the necessity of using primary muscle cells to discover physiologically relevant drug targets that regulate the expression of DUX4.

DUX4 has historically been regarded as being challenging to detect in FSHD muscle. Its expression in primary myoblasts from patients with FSHD has been shown to be stochastic. Studies have reported that only 1 in 1000 or 1 in 200 nuclei is DUX4 positive in proliferating FSHD myoblasts and during myoblast differentiation, respectively. Due to this particularly low abundance of DUX4, detection of DUX4 protein has been reported to be a technical challenge. While primary FSHD muscle cells have been used extensively in the FSHD literature, none of the reports appear to be applicable beyond a bench scale level. The limitations posed by using primary cells and the recognised complexity of detecting the low levels of endogenous DUX4 illustrate the challenges associated with applying primary FSHD muscle cells to higher throughput formats. Although DUX4 expression increases upon in vitro differentiation of proliferating FSHD myoblasts into multinucleated myotubes, the levels remain low and the dynamic variability is widely accepted to be extremely challenging for robust large-scale screening approaches (Campbell et al., 2017).

Compound for Use

In a first aspect the invention provides a casein kinase 1 (CK1) inhibitor for use in the treatment of a disease or condition associated with (undue) DUX4 expression, wherein the casein kinase 1 inhibitor reduces DUX4 expression. Such a CK1 inhibitor is referred to herein as a CK1 inhibitor for use according to the invention. CK1 inhibitors are known in the art and are described in more detail later herein.

The medical use herein described is formulated as a compound as defined herein for use as a medicament for treatment of the stated condition(s) (e.g. by administration of an effective amount of the compound), but could equally be formulated as i) a method of treatment of the stated condition(s) using a compound as defined herein comprising a step of administering to a subject an effective amount of the compound, ii) a compound as defined herein for use in the manufacture of a medicament to treat the stated condition(s), wherein preferably the compound is to be administered in an effective amount, and iii) use of a compound as defined herein for the treatment of the stated condition(s), preferably by administering an effective amount. Such medical uses are all envisaged by the present invention. Preferred subjects are subjects in need of treatment. Treatment preferably leads to delay, amelioration, alleviation, stabilization, cure, or prevention of a disease or condition. In other words, a compound for use according to the invention can be a compound for the treatment, delay, amelioration, alleviation, stabilization, cure, or prevention of the stated disease or condition.

The CK1 inhibitor for use according to the invention reduces DUX4 expression. This DUX4 expression is preferably the overall DUX4 expression of the subject that is treated. DUX4 expression can be determined using methods known in the art, or exemplified in the examples. For example, DUX4 expression can be determined using PCR techniques such as RT-PCR, or using immunostaining, mass spectrometry, or ELISA, for example on a sample containing cells or cell extracts, preferably obtained from the subject. In this context, a reduction is preferably a reduction as compared to either a predetermined value, or to a reference value. A preferred reference value is a reference value obtained by determining DUX4 expression in an untreated sample containing cells or cell extracts. This untreated sample can be from the same subject or from a different and healthy subject, more preferably it is a sample that was obtained in the same way, thus containing the same type of cells. Conveniently, both the test sample and the reference sample can be part of a single larger sample that was obtained. Alternately, the test sample was obtained from the subject before treatment commenced. A highly preferred reference value is the expression level of DUX4 in a sample obtained from a subject prior to the first administration of the casein kinase 1 inhibitor according to the invention. Another preferred reference value is a fixed value that represents an absence of DUX4 expression.

A reduction of DUX4 expression preferably means that expression is reduced by at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%. If expression of DUX4 is reduced by for example 100%, it may be that expression of DUX4 can no longer be detected. Reduction can be assessed at the protein level, for example through immunostaining, ELISA, or mass spectrometry, or it can be assessed at the mRNA level, for example through PCR techniques such as RT-PCR. In preferred embodiments, the invention provides a casein kinase 1 inhibitor for use according to the invention, wherein the reduction of DUX4 expression is determined using PCR or immunostaining, wherein a preferred PCR technique is RT-PCR. In preferred embodiments the invention provides a casein kinase 1 inhibitor for use according to the invention, wherein DUX4 expression is reduced by at least 20%, 40%, 60%, 80%, or more, more preferably by at least 30%, 40%, 60%, 80%, or more. In further preferred embodiments, DUX4 expression is reduced by at least 10%. In further preferred embodiments, DUX4 expression is reduced by at least 20%. In further preferred embodiments, DUX4 expression is reduced by at least 30%. In further preferred embodiments, DUX4 expression is reduced by at least 40%. In further preferred embodiments, DUX4 expression is reduced by at least 50%. In further preferred embodiments, DUX4 expression is reduced by at least 60%. In further preferred embodiments, DUX4 expression is reduced by at least 70%. In further preferred embodiments, DUX4 expression is reduced by at least 80%. In further preferred embodiments, DUX4 expression is reduced by at least 90%. In further preferred embodiments, DUX4 expression is reduced by at least 95%. In the most preferred embodiments, DUX4 expression is reduced by about 100%, preferably by 100%.

In preferred embodiments, the invention provides a casein kinase 1 inhibitor for use according to the invention, wherein the casein kinase 1 inhibitor reduces DUX4 expression in muscle cells, immune cells, or cancer cells, preferably in muscle cells or immune cells, most preferably in muscle cells. Preferred muscle cells are myoblasts, satellite cells, myotubes, and myofibers. Preferred immune cells are B cells, T cells, dendritic cells, neutrophils, natural killer cells, granulocytes, innate lymphoid cells, megakaryocytes, myeloid-derived suppressor cells, monocytes/macrophages, and thymocytes, and optionally mast cells. Other preferred cells are platelets and red blood cells. In other embodiments, DUX4 expression is reduced in cancer cells.

In preferred embodiments the invention provides the CK1 inhibitors for use according to the invention, wherein said disease or condition associated with DUX4 expression is a muscular dystrophy or cancer, preferably wherein said disease or condition associated with DUX4 expression is a muscular dystrophy, most preferably facioscapulohumeral muscular dystrophy (FSHD).

In this context, a preferred muscular dystrophy is FSHD; a preferred cancer is prostate cancer (WO2014081923), multiple myeloma (US20140221313), lung cancer (Lang et al., 2014, DOI: 10.14205/2310-8703.2014.02.01.1), colon cancer (Paz et al., 2003, DOI: 10.1093/hmg/ddg226) sarcoma, or leukemia; a preferred sarcoma is small round cell sarcoma (Oyama et al., 2017 DOI: 10.1038/s41598-017-04967-0; Bergerat et al., 2017, DOI: 10.1016/j.prp.2016.11.015; Chebib and Jo, 2016, DOI: 10.1002/cncy.21685); a preferred leukemia is acute lymphoblastic leukemia (ALL), more particularly B-cell precursor ALL (Yasuda et al., 2016, doi: 10.1038/ng.3535; Lilljebjörn & Fioretos, 2017, DOI: 10.1182/blood-2017-05-742643; Zhang et al., 2017, DOI:10.1038/ng.3691).

Accordingly, in preferred embodiments, the invention provides the CK1 inhibitors for use according to the invention, wherein said disease or condition associated with DUX4 expression is a muscular dystrophy or cancer, preferably wherein said disease or condition associated with DUX4 expression is FSHD, prostate cancer, multiple myeloma, lung cancer, colon cancer (preferably colorectal carcinoma), sarcoma (preferably small round cell sarcoma), leukemia (preferably acute lymphoblastic leukemia, more preferably B-cell precursor acute lymphoblastic leukemia), preferably said disease or condition associated with DUX4 expression is FSHD. In more preferred embodiments, the invention provides the CK1 inhibitors for use according to the invention, wherein said disease or condition associated with DUX4 expression is a muscular dystrophy or cancer, preferably wherein said disease or condition associated with DUX4 expression is FSHD or cancer, wherein cancer is preferably prostate cancer, multiple myeloma, lung cancer, colon cancer (preferably colorectal carcinoma), sarcoma (preferably small round cell sarcoma), leukemia (preferably acute lymphoblastic leukemia, more preferably B-cell precursor acute lymphoblastic leukemia), wherein cancer is more preferably sarcoma, most preferably small round cell sarcoma.

In a preferred embodiment, the invention provides the CK1 inhibitors for use according to the invention, wherein said disease or condition associated with DUX4 expression is cancer, wherein cancer is preferably prostate cancer, multiple myeloma, lung cancer, colon cancer (preferably colorectal carcinoma), sarcoma (preferably small round cell sarcoma), leukemia (preferably acute lymphoblastic leukemia, more preferably B-cell precursor acute lymphoblastic leukemia), wherein cancer is more preferably sarcoma, most preferably small round cell sarcoma.

Other DUX4 targets are known as "cancer testis antigens" (CTAs), which are genes that are normally expressed only in testis, but which are de-repressed in some cancers, eliciting an immune response. These observations imply that DUX4 de-repression in cancers mediates the activation of HSATII, CTAs and/or THE1B promoters (Young et al., 2013, doi: 10.1371/journal.pgen.1003947). In line with this, Dmitriev et al. (2014, DOI: 10.1111/jcmm.12182) demonstrate a similarity between FSHD and cancer cell expression profiles, suggesting a common step in the pathogenesis of these diseases.

Casein Kinase 1 Inhibitor

Casein kinase 1 inhibitors are known in the art. Preferably, in the context of this invention, a casein kinase 1 inhibitor for use according to the invention is of general structural formula (1a), (1b), (2a), (2b), or (3):

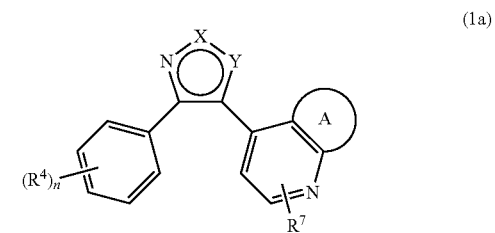
(1a)

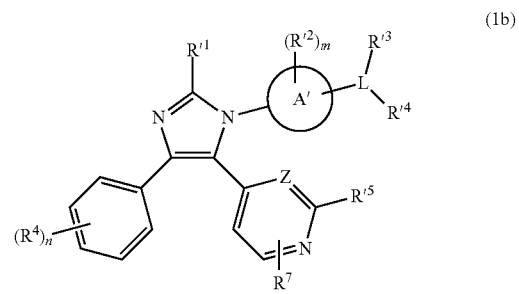
(1b)

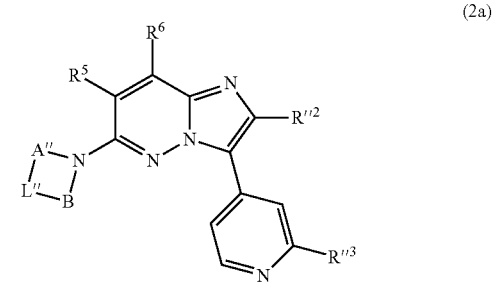
(2a)

-continued

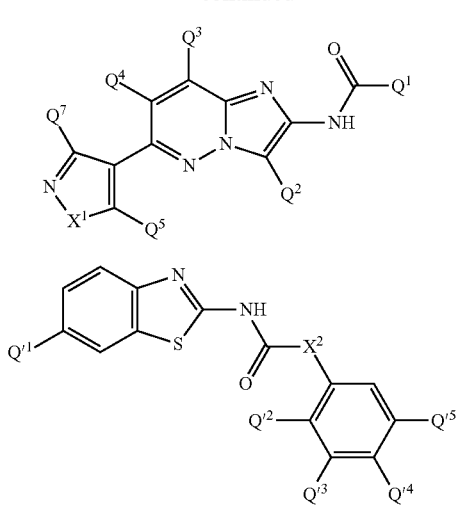

(2b)

(3)

wherein X and Y are independently =N—, —NR¹—, CR¹, or —S—, provided that at least one of X and Y is CR¹, ring A is absent (so effectively it is two H) or is a 4- to 7-membered cycloalkyl or heterocycloalkyl or a 5- to 6-membered heteroaryl, wherein up to 2 carbon atoms are replaced with a heteroatom selected from =N—, —NR²—, —O—, —S— and any remaining carbon atom may be substituted with R³ as valency allows; preferably, ring A is a 4- to 7-membered cycloalkyl or heterocycloalkyl or a 5- to 6-membered heteroaryl, wherein up to 2 carbon atoms are replaced with a heteroatom selected from =N—, —NR²—, —O—, —S— and any remaining carbon atom may be substituted with R³ as valency allows;

each R¹ is independently H, $C_{1-4}$alkyl, $C_{3-6}$cycloalkyl, —CF₃, —(CH₂)$_{1-3}$ CF₃, 4- to 10-membered aryl, 4- to 10-membered heteroaryl, 4- to 10-membered heterocycloalkyl, wherein said aryl, heteroaryl, or heterocycloalkyl may be substituted with one, two, or three substituents independently selected from halogen, OH, oxo, cyano, —SO₂CH₃, carboxylic acid that is optionally esterified with methanol or ethanol, carboxamide, nitro, $C_{1-6}$ alkoxy, $C_{1-6}$ alkyl, or $C_{1-6}$ alkyl-O—$C_{1-6}$alkyl; preferably, each R¹ is independently H, $C_{1-4}$alkyl, $C_{3-6}$cycloalkyl, —CF₃, —(CH₂)$_{1-3}$—CF₃, 4- to 10-membered heterocycloalkyl, wherein said heterocycloalkyl may be substituted with up to two substituents independently selected from halogen, OH, oxo, cyano, $C_{1-6}$ alkyl, or $C_{1-6}$ alkyl-O—$C_{1-6}$alkyl;

Each R² is independently H, $C_{1-6}$ alkyl, $C_{4-10}$-bicycloalkyl, —(CH₂)$_t$—CN, —SO₂—$C_{1-6}$ alkyl, —SO₂(CH₂)$_t$ $C_{3-6}$cycloalkyl, —$C_{1-6}$ alkyl-O—$C_{1-6}$alkyl, —$C_{1-6}$ alkyl-C(O)O—$C_{1-6}$ alkyl, —$C_{3-6}$cycloalkyl-C(O)O—$C_{1-6}$ alkyl, —C(O)—(O)$_u$—$C_{1-6}$ alkyl, —C(O)—$C_{1-6}$ alkyl-O—$C_{1-6}$alkyl, —C(O)—(O)$_u$—(CH2)$_t$—($C_{6-10}$aryl), —(CH₂)$_t$ —($C_{6-10}$aryl), —C(O)—(O)$_u$—(CH₂)$_t$-(5- to 10-membered heteroaryl), —(CH₂)$_t$—C(O)—NR⁵R⁶, —(CH₂)$_t$-(5- to 10-membered heteroaryl), —C(O)—(O)$_u$—(CH₂)$_t$-(3- to 10-membered heterocycloalkyl), —(CH₂)$_t$-(4- to 10-membered heterocycloalkyl), —C(O)—(O)$_u$—(CH₂)$_t$-(3- to 10-membered cycloalkyl), or —(CH₂)$_t$-(3- to 10-membered cycloalkyl), wherein said aryl, heteroaryl, cycloalkyl, and heterocycloalkyl of R² may be substituted with up to two substituents independently selected from halogen, OH, cyano, $C_{1-6}$ alkyl, or $C_{1-6}$ alkyl-O—$C_{1-6}$ alkyl, and wherein any alkyl, cycloalkyl, and heterocycloalkyl of R² may be further substituted with oxo where valency allows;

each R³ is independently absent, $C_{1-3}$ alkyl, halogen, oxo, —NR⁵R⁶, or —OR⁵;

each R⁴ is independently halogen, —CF₃, $C_{1-3}$ alkyl, —(CH₂)$_t$—$C_{3-4}$cycloalkyl, —(CH₂)$_t$—O—$C_{1-3}$ alkyl, —(CH₂)$_t$-cyano, or —(CH₂)$_t$-hydroxy, wherein a halogen is preferably F and is preferably para to the five-membered ring comprising X and Y, wherein $C_{1-3}$ alkyl is preferably methyl and is preferably meta to the five-membered ring comprising X and Y; preferably, each R⁴ is independently halogen, —CF₃, $C_{1-3}$ alkyl, —(CH₂)$_t$—$C_{3-4}$cycloalkyl, —(CH₂)$_t$—O—$C_{1-3}$ alkyl, —(CH₂)$_t$-cyano, or —(CH₂)$_t$-hydroxy;

each R⁵ is independently H or $C_{1-6}$ alkyl;
each R⁶ is independently H or $C_{1-6}$ alkyl;
R⁷ is H, halogen, or $C_{1-3}$ alkyl;
n is 0, 1, or 2;
each t is independently 0, 1, or 2;
each u is independently 0 or 1;
and wherein A' is a 4- to 7-membered cycloalkyl, a nitrogen-containing 4- to 7-membered heterocycloalkyl, or alternatively A' can be directly fused to the ring to which it is attached through R'¹; preferably, A' is a nitrogen-containing 4- to 7-membered heterocycloalkyl, or alternatively A' can be directly fused to the ring to which it is attached through R'¹;

L is $C_{1-3}$ alkyl;
R'¹ is hydrogen, $C_{1-3}$ alkyl, or $C_{3-4}$cycloalkyl;
each R'² is independently $C_{1-3}$ alkyl, fluorine, hydroxyl, $C_{1-3}$ alkoxy, or cyano;
R'³ is hydrogen, $C_{1-3}$ alkyl, or $C_{3-4}$cycloalkyl;
R'⁴ is a 5- to 10-membered heteroaryl with 1 to 3 heteroatoms, optionally substituted with 1 to 3 R⁴ substituents;
R'⁶ is hydrogen or —N(R⁸)₂;
Z is N or —CR⁹;
each R⁸ is independently hydrogen or $C_{1-3}$ alkyl;
R⁹ is hydrogen, $C_{1-3}$ alkyl, or halogen;
m is 0, 1 or 2;
q is 1, 2, or 3;
and wherein R"² represents an aryl group optionally substituted with one or more substituents selected from halogen, $C_{1-6}$ alkyl, $C_{1-6}$ alkyloxy, $C_{1-6}$ alkylthio, $C_{1-6}$ fluoroalkyl, $C_{1-6}$ fluoroalkyloxy and —CN;

R"³ represents H, $C_{1-3}$ alkyl, —NR"⁴R"⁵, hydroxyl, or $C_{1-4}$alkyloxy;

A" represents $C_{1-7}$-alkylene optionally substituted with one or two R$^a$;

B represents $C_{1-7}$-alkylene optionally substituted with R$^b$;

L" represents either N substituted with R$^c$ or R$^d$, or C substituted with R$^{e1}$ and R$^d$ or with two groups R$^{e2}$;

the carbon atoms of A" and B being optionally substituted with one or more groups R$^f$, which may be identical to or different than each other;

R$^a$, R$^b$ and R$^c$ are defined such that:
 two groups R$^a$ may together form $C_{1-6}$alkylene;
 R$^a$ and R$^b$ may together form a bond or $C_{1-6}$alkylene;
 R$^a$ and R$^c$ may together form a bond or $C_{1-6}$alkylene;
 R$^b$ and R$^c$ may together form a bond or $C_{1-6}$ alkylene;
 R$^d$ represents a group selected from H, $C_{1-6}$ alkyl, $C_{3-7}$cycloalkyl, $C_{3-7}$cycloalkyl-$C_{1-6}$alkyl, $C_{1-6}$ alkylthio-$C_{1-6}$alkyl, $C_{1-6}$ alkyloxy-$C_{1-6}$alkyl, $C_{1-6}$ fluoroalkyl, benzyl, $C_{1-6}$ acyl, and hydroxy-$C_{1-6}$alkyl;
 R$^{e1}$ represents —NR"⁴R"⁵ or a cyclic monoamine optionally comprising an oxygen atom, the cyclic monoamine being optionally substituted with one or more substituents selected from F, $C_{1-6}$alkyl, $C_{1-6}$ alkyloxy, and hydroxyl;

two groups $R^{e2}$ form, with the carbon atom that bears them, a cyclic monoamine optionally comprising an oxygen atom, this cyclic monoamine being optionally substituted with one or more $R^f$, which may be identical to or different than each other;

$R^f$ represents $C_{1-6}$ alkyl, $C_{3-7}$cycloalkyl, $C_{3-7}$cycloalkyl $C_{1-6}$ alkyl, $C_{1-6}$ alkyloxy-$C_{1-6}$alkyl, hydroxy-$C_{1-6}$alkyl, $C_{1-6}$ fluoroalkyl or benzyl;

$R''^4$ and $R''^5$ each independently represent H, $C_{1-4}$alkyl, $C_{3-7}$cycloalkyl, or $C_{3-7}$cycloalkyl-$C_{1-6}$alkyl;

and wherein $X^1$ is selected from 0 and $NQ^6$; provided when $X^1$ is $NQ^6$, $Q^5$ and $Q^6$ together with the nitrogen atom and the adjacent carbon atom to which they are respectively attached form a heterocyclic ring comprising carbon atoms and zero to 3 additional heteroatoms selected from N, $NQ^8$, O, S and substituted with 1-5 $Q^{10}$;

$Q^1$ is $C_{1-4}$alkyl optionally substituted with halogen, OH, CN, and $NQ^aQ^a$, or $Q^1$ is $-(CQ^dQ^d)_r$-carbocyclyl substituted with 0-5 $Q^{11}$, and $-(CQ^dQ^d)_r$-heterocyclyl comprising carbon atoms and 1 to 4 heteroatoms selected from N, $NQ^9$, O, S, and substituted with 0-5 $Q^{11}$;

$Q^2$ is selected from H, $C_{1-4}$alkyl, halogen, CN, aryl, and heteroaryl;

$Q^3$ is selected from H and $C_{1-4}$alkyl;

$Q^4$ is selected from H, $C_{1-4}$alkyl halogen, and CN;

$Q^5$ is selected from H, $C_{1-4}$alkyl substituted with 0-4 $Q^e$, $-(CH_2)_r-C_{3-6}$ carbocyclyl substituted with 0-4 $Q^e$, and $-(CH_2)_r$-heterocyclyl comprising carbon atoms and 1 to 3 heteroatoms selected from N, O, S, and substituted with 0-4 $Q^e$;

$Q^7$ is aryl substituted with 0-3 $Q^e$;

$Q^8$ is selected from H, $C_{1-4}$alkyl substituted with 0-3 $Q^e$, $-(CH_2)_rCN$, $-(CH_2)_rOQ^b$, $-(CH_2)_rS(O)_pQ^c$, $-(CH_2)_rC(=O)Q^b$, $-(CH_2)_rNQ^aQ^a$, $-(CH_2)_rC(=O)NQ^aQ^a$, $-(CH_2)_rC(=O)-C_{1-4}$alkyl substituted with 0-3 $Q^e$, $-(CH_2)_rNQ^aC(=O)Q^b$, $-(CH_2)_rNQ^aC(=O)OQ^b$, $-(CH_2)_rOC(=O)NQ^aQ^a$, $-(CH_2)_rNQ^aC(=O)NQ^aQ^a$, $-(CH_2)_rC(=O)OQ^b$, $-(CH_2)_rS(O)_2NQ^aQ^a$, $-(CH_2)_rNQ^aS(O)_2NQ^aQ^a$, $-(CH_2)_rNQ^aS(O)_2Q^c$, $-(CH_2)_r$-carbocyclyl substituted with 0-3 $Q^e$, and $-(CH_2)_r$-heterocyclyl substituted with 0-3 $Q^e$;

$Q^9$ is selected from H, $-C(=O)Q^b$, $C_{1-6}$alkyl substituted with 0-5 $Q^e$, $-(CH_2)_r-C_{3-6}$carbocyclyl substituted with 0-5 $Q^e$, and $-(CH_2)_r$-heterocyclyl substituted with 0-5 $Q^e$;

$Q^{10}$ is selected from H, $C_{1-6}$ alkyl substituted with 0-3 $Q^e$, $-(CH_2)_rNQ^aQ^a$, $-(CH_2)_rC(=O)Q^b$, $-(CH_2)_rC(=O)OQ^b$, $-(CH_2)_rC(=O)NQ^aQ^a$, $-S(O)_pQ^c$, $-(CH_2)C_{3-6}$carbocyclyl substituted with 0-3 $Q^e$, and $-(CH_2)_r$-heterocyclyl substituted with 0-3 $Q^e$;

each $Q^{11}$ is independently selected from H, halogen, =O, CN, $NO_2$, $-OQ^b$, $-S(O)^pQ^c$, $-C(=O)Q_b$, $-(CQ^dQ^d)_rNQ^aQ^a$, $-(CQ^dQ^d)_rC(=O)NQ^aQ^a$, $-NQ^aC(=O)Q^b$, $-NQ^aC(=O)OQ^b$, $-OC(=O)NQ^aQ^a$, $-NQ^aC(=O)NQ^aQ^a$, $-(CQ^dQ^d)_rC(=O)OQ^b$, $-S(O)_2NQ^aQ^a$, $-NQ^aS(O)_2NQ^aQ^a$, $-NQ^aS(O)_2Q^c$, $C_{1-6}$ alkyl substituted with 0-5 $Q^e$, $-(CQ^dQ^d)_r-C_{3-6}$carbocyclyl substituted with 0-5 $Q^e$, and $-(CQ^dQ^d)_r$-heterocyclyl substituted with 0-5 $Q^e$;

each $Q^a$ is independently selected from H, CN, $C_{1-6}$alkyl substituted with 0-5 $Q^e$, $C_{2-6}$alkenyl substituted with 0-5 $Q^e$, $C_{2-6}$alkynyl substituted with 0-5 $Q^e$, $-(CH_2)_r-C_{3-10}$carbocyclyl substituted with 0-5 $Q^e$, and $-(CH_2)_r$-heterocyclyl substituted with 0-5 $Q^e$; or two instances of $Q^a$ together with the nitrogen atom to which they are both attached form a heterocyclic ring substituted with 0-5 $Q^e$;

each $Q^b$ is independently selected from H, $C_{1-6}$alkyl substituted with 0-5 $Q^e$, $C_{2-6}$alkenyl substituted with 0-5 $Q^e$, $C_{2-6}$alkynyl substituted with 0-5 $Q^e$, $-(CH_2)_r-C_{3-10}$carbocyclyl substituted with 0-5 $Q^e$, and $-(CH_2)_r$-heterocyclyl substituted with 0-5 $Q^e$;

each $Q^c$ is independently selected from $C_{1-6}$alkyl substituted with 0-5 $Q^e$, $C_{2-6}$alkenyl substituted with 0-5 $Q^e$, $C_{2-6}$alkynyl substituted with 0-5 $Q^e$, $C_{3-6}$carbocyclyl substituted with 0-5 $Q^e$, and heterocyclyl substituted with 0-5 $Q^e$;

each $Q^d$ is independently selected from H and $C_{1-4}$alkyl substituted with 0-5 $Q^e$;

each $Q^e$ is independently selected from $C_{1-6}$alkyl substituted with 0-5 $Q^f$, $C_{2-6}$alkenyl, $C_{2-6}$ alkynyl, $-(CH_2)_r-C_{3-6}$cycloalkyl, halogen, CN, $NO_2$, =O, $CO_2H$, $-(CH_2)_rOQ^f$, $SQ^f$, and $-(CH_2)_rNQ^fQ^f$;

each $Q^f$ is independently selected from H, F, $C_{3-6}$cycloalkyl, and phenyl, or two instances of $Q^f$ together with the nitrogen atom to which they are both attached form a heterocyclic ring optionally substituted with $C_{1-4}$alkyl;

each p is independently 0, 1, or 2; and each r is independently 0, 1, 2, 3, or 4, and wherein $X^2$ is selected from $-NH-$, $-CH_2-$, $-CH(Ph)$-, $-CH_2CH_2-$, $-CH_2CH(Ph)$-, $-CH=CH-$, $-CH_2OCH_2-$, $-CH_2NHC(O)-$, $-CH_2NHC(O)CH(Ph)$- and $-CH_2NHC(O)CH_2-$, $Q'^1$ is selected from $Q'^6$, halogen, $-CF_3$, $-OCF_3$, $-OQ'^6$, $-CO_2Q'^6$, $-SO_2N(Q'^6)_2$, and $-NO_2$;

$Q'^2$, $Q'^3$, $Q'^4$, and $Q'^5$ are independently selected from H, halogen, $C_{1-6}$ alkoxy, $-NH_2$, $-NHQ'6$, $-CN$, $-NO_2$, $-OCF_3$, and $-CO_2Q'^6$; wherein $Q'^6$ is selected from H and $C_{1-6}$ alkyl; and wherein when $X^2$ is $-CH(Ph)$-, $-CH_2CH(Ph)$- or $-CH_2NHC(O)CH(Ph)$-, then $Q'^2$, $Q'^3$, $Q'^4$, and $Q'^5$ are H, or isomers or pharmaceutically acceptable salts thereof.

A CK1 inhibitor for use according to the invention can also be SR-3029.

SR-3029

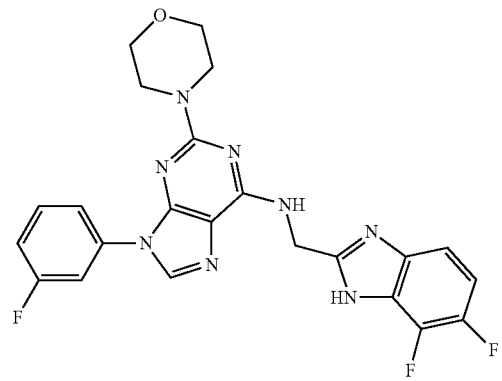

In preferred embodiments, the CK1 inhibitor for use according to the invention is of general formula (Ia) or (Ib), or isomers or pharmaceutically acceptable salts thereof, wherein X, Y, A, $R^1$, $R^2$, $R^3$, $R^4$, $R^5$, $R^6$, $R^7$, n, t, u, A', L, $R'^1$, $R'^2$, $R'^3$, $R'^4$, $R'^5$, Z, $R^8$, $R^9$, m, and q are as defined above. In a further preferred embodiment, it is of general formula (Ia), or isomers or pharmaceutically acceptable salts thereof, wherein X, Y, A, $R^1$, $R^2$, $R^3$, $R^4$, $R^5$, $R^6$, $R^7$, n, t, u, A', L, $R'^1$, $R'^2$, $R'^3$, $R'^4$, $R'^5$, Z, $R^8$, $R^9$, m, and q are as defined above. In a further preferred embodiment, it is of general formula (Ib), or isomers or pharmaceutically acceptable salts thereof, wherein X, Y, A, $R^1$, $R^2$, $R^3$, $R^4$, $R^5$, $R^6$, $R^7$, n, t, u, A', L, $R'^1$, $R'^2$, $R'^3$, $R'^4$, $R'^5$, Z, $R^8$, $R^9$, m, and q are as defined above. CK1 inhibitors of this class are known per se in the art and have their structure and synthesis described in more detail in, for example, WO2011051858, WO2012085721, and WO2015119579.

CK1 inhibitors of this class comprise an azole core. In preferred embodiments of this aspect, the invention provides casein kinase 1 inhibitor for use according to the invention, wherein the casein kinase 1 inhibitor is from the class comprising an azole core. More preferably, these CK1 inhibitors for use comprise a 4-aryl-5-heteroaryl-1-heterocycloalkyl-imidazole moiety. Preferably, for these inhibitors, a single $R^4$ is present, para to the azole core; more preferably this $R^4$ is F. Accordingly, in further more preferred embodiments, the casein kinase 1 inhibitor for use according to the invention comprises an azole core linked to a 4-halophenyl moiety, preferably a 4-fluorophenyl moiety. Highly preferred compounds comprising an azole core are compounds D, E, F, and G as shown in table 3; compound D is even more preferred.

In preferred embodiments, the CK1 inhibitor for use according to the invention is of general formula (2a) or (2b), or isomers or pharmaceutically acceptable salts thereof, wherein $R^5$, $R^6$, $R''^2$, $R''^3$, A'', B, L'', $R^a$, $R^b$, $R^c$, $R^d$, $R^{e1}$, $R^{e2}$, $R^f$, $R'''^4$, $R'''^5$, $X^1$, $Q^1$, $Q^2$, $Q^3$, $Q^4$, $Q^5$, $Q^6$, $Q^7$, $Q^8$, $Q^9$, $Q^{10}$, $Q^{11}$, $Q^a$, $Q^b$, $Q^c$, $Q^d$, $Q^e$, $Q^f$, r, and P are as defined above. In a further preferred embodiment, it is of general formula (2a) or isomers or pharmaceutically acceptable salts thereof, wherein $R^5$, $R^6$, $R''^2$, $R''^3$, A'', B, L'', $R^a$, $R^b$, $R^c$, $R^d$, $R^{e1}$, $R^{e2}$, $R^f$, $R'''^4$, $R'''^5$, $X^1$, $Q^1$, $Q^2$, $Q^3$, $Q^4$, $Q^5$, $Q^6$, $Q^7$, $Q^8$, $Q^9$, $Q^{10}$, $Q^{11}$, $Q^a$, $Q^b$, $Q^c$, $Q^d$, $Q^e$, $Q^f$, P, and r are as defined above. In a further preferred embodiment, it is of general formula (2b) or isomers or pharmaceutically acceptable salts thereof, wherein $R^5$, $R^6$, $R''^2$, $R''^3$, A'', B, L'', $R^a$, $R^b$, $R^c$, $R^d$, $R^{e1}$, $R^{e2}$, $R^f$, $R'''^4$, $R'''^5$, $X^1$, $Q^1$, $Q^2$, $Q^3$, $Q^4$, $Q^5$, $Q^6$, $Q^7$, $Q^8$, $Q^9$, $Q^{10}$, $Q^{11}$, $Q^a$, $Q^b$, $Q^c$, $Q^d$, $Q^e$, $Q^f$, P, and r are as defined above. CK1 inhibitors of this class are known per se in the art and have their structure and synthesis described in more detail in, for example, WO2009016286 and WO2015195880.

CK1 inhibitors of this class comprise a cyclo-3-pyrid-4-yl)imidazo[1,2-b]pyridazine core. In preferred embodiments of this aspect, the invention provides casein kinase 1 inhibitor for use according to the invention, wherein the casein kinase 1 inhibitor is from the class comprising a cyclo-3-pyrid-4-yl)imidazo[1,2-b]pyridazine core. In further preferred embodiments, the casein kinase 1 inhibitor for use according to the invention comprises an azole core or comprises a cyclo-3-pyrid-4-yl)imidazo[1,2-b]pyridazine core. In further preferred embodiments, the casein kinase 1 inhibitor for use according to the invention is of general formula (1a), (1b), (2a), or (2b), wherein X, Y, A, $R^1$, $R^2$, $R^3$, $R^4$, $R^5$, $R^6$, $R^7$, n, t, u, A', L, $R'^1$, $R'^2$, $R'^3$, $R'^4$, $R'^5$, Z, $R^8$, $R^9$, m, q, $R''^2$, $R''^3$, A'', B, L'', $R^a$, $R^b$, $R^c$, $R^d$, $R^{e1}$, $R^{e2}$, $R^f$, $R'''^4$, $R'''^5$, $X^1$, $Q^1$, $Q^2$, $Q^3$, $Q^4$, $Q^5$, $Q^6$, $Q^7$, $Q^8$, $Q^9$, $Q^{10}$, $Q^{11}$, $Q^a$, $Q^b$, $Q^c$, $Q^d$, $Q^e$, $Q^f$, r, and P are as defined above.

In preferred embodiments, the CK1 inhibitor for use according to the invention is of general formula (3) or isomers or pharmaceutically acceptable salts thereof, wherein $X^2$, $Q'^1$, $Q'^2$, $Q'^3$, $Q'^4$, $Q'^5$, and $Q'^6$ are as defined above. CK1 inhibitors of this class are known in the art per se and have their structure and synthesis described in more detail in, for example, EP2949651. When a Csk1 inhibitor is of general formula (3), $X^2$ is preferably —$CH_2$—, —$CH_2CH_2$—, —CH(Ph)-, or —NH—, most preferably —$CH_2$—; Q'1 is preferably —$CF_3$, halogen, or $C_{1-6}$alkyl, more preferably —$CF_3$; $Q'^2$, $Q'^3$, $Q'^4$, and $Q'^5$ are preferably independently selected from H, halogen, and $C_{1-5}$-alkoxy. More preferably, when a CK1 inhibitor is of general formula (3), $X^2$ is —$CH_2$— and $Q'^1$ is —$CF_3$.

Structures of exemplary CK1 inhibitors are shown in table 3. In further preferred embodiments, the invention provides the CK1 inhibitor for use according to the invention, wherein the casein kinase 1 inhibitor is selected from the group consisting of compounds A, B, C, D, E, F, G, H, I, J, K, L, M, N, O, SR-3029, PF-670462, and PF-5006739. Compound O is also known as TA-01. More preferably, the casein kinase 1 inhibitor is selected from the group consisting of compounds A, B, C, D, E, F, G, H, O, SR-3029, PF-670462, and PF-5006739. Even more preferably, the casein kinase 1 inhibitor is selected from the group consisting of compounds A, D, F, G, H, O, SR-3029, PF-670462, and PF-5006739. Even more preferably, the casein kinase 1 inhibitor is selected from the group consisting of compounds A, D, F, G, H, SR-3029, PF-670462, and PF-5006739. Most preferably, the casein kinase 1 inhibitor is selected from the group consisting of compounds A, D, F, G, H, SR-3029, and PF-5006739. It is also highly preferred that the casein kinase 1 inhibitor be compound D. It is also highly preferred that the casein kinase 1 inhibitor is selected from the group consisting of compounds A, B, and H, more preferably it is compound H.

In other embodiments, the CK1 inhibitor for use according to the invention is an inhibitory antibody, an antisense oligonucleotide, or an oligonucleotide that prevents expression of CK1.

The various isoforms of casein kinase 1 are known to have different functions. Within the set of known isoforms, CK1δ and CK1ε are preferred targets for the CK1 inhibitors according to the invention. These two isoforms are known to be closely related to one another. For example, CK1δ and CK1ε were thought to be generally redundant in circadian cycle length and protein stability, but were later revealed to have slightly different functions (Etchegaray J P et al., 2009, DOI:10.1128/MCB.00338-09). Due to their physiological importance, and the known efficacy of the CK1 inhibitors for use in the present invention, preferred embodiments of the invention provide a casein kinase 1 inhibitor for use according to the invention, wherein the casein kinase inhibitor inhibits at least casein kinase 1δ or casein kinase 1ε. Optionally, the casein kinase inhibitor is specific for casein kinase 1δ or for casein kinase 1ε. Furthermore, in more preferred embodiments the invention provides a casein kinase 1 inhibitor for use according to the invention, wherein the casein kinase inhibitor at least inhibits, and optionally is specific for, casein kinase 1δ. In other more preferred embodiments the invention provides a casein kinase 1 inhibitor for use according to the invention, wherein the casein kinase inhibitor at least inhibits, and optionally is specific for, casein kinase 1ε. In other embodiments the invention provides a casein kinase 1 inhibitor for use according to the invention, wherein the casein kinase inhibitor at least inhibits, and optionally is specific for, casein kinase 1α. In other embodiments the invention provides a casein kinase 1 inhibitor for use according to the invention, wherein the casein kinase inhibitor at least inhibits, and optionally is specific for, casein kinase 1β. In other embodiments the invention provides a casein kinase 1 inhibitor for use according to the invention, wherein the casein kinase inhibitor at least inhibits, and optionally is specific for, casein kinase 1γ1, 1γ2, and/or 1γ3. It is to be understood in this context that a CK1 inhibitor is specific for a particular isoform when it at least partially inhibits that particular isoform. Preferably, it inhibits that particular isoform more efficiently than other isoforms.

CK1 inhibitors suitable for use in the invention preferably have an $IC_{50}$ on a casein kinase of at most 650 nM, preferably of at most 500 nM, more preferably of at most 400 nM, even more preferably of at most 300 nM, still more preferably of at most 250 nM, still more preferably of at most 200 nM, most preferably of at most 100 nM. In preferred embodiments, the CK1 inhibitor has an $IC_{50}$ on at least casein kinase 1δ or casein kinase 1ε of at most 450 nM, more preferably of at most 400 nM, even more preferably of at most 350 nM, more preferably still of at most 200 nM, even more preferably still of at most 100 nM, most preferably of at most 50 nM. In most preferred embodiments the CK1 inhibitor has an $IC_{50}$ on casein kinase 1δ of at most 350 nM, preferably at most 100 nM, more preferably at most 35 nM, most preferably at most 25 nM. $IC_{50}$ values for CK1 can be determined using any method known in the art, for example as described in WO2011051858, WO2015119579, EP2949651, or US2005/0131012. Suitable assays can use a peptide substrate and a readout method, for example using the Kinase-Glo assay (Promega, part # V672A).

Composition

In a further aspect, the invention provides a composition comprising at least one CK1 inhibitor, and a pharmaceutically acceptable excipient, for use according to the invention. Such a composition is referred to herein as a composition for use according to the invention. Preferred compositions for use according to the invention are pharmaceutical compositions. In preferred embodiments, the composition for use according to the invention is formulated for oral, sublingual, parenteral, intravascular, intravenous, subcutaneous, or transdermal administration, optionally for administration by inhalation; preferably for oral administration. More features and definitions of administration methods are provided in the section on formulation and administration.

Formulation and Administration

The compositions comprising the compounds as described above, can be prepared as a medicinal or cosmetic preparation or in various other media, such as foods for humans or animals, including medical foods and dietary supplements. A "medical food" is a product that is intended for the specific dietary management of a disease or condition for which distinctive nutritional requirements exist. By way of example, but not limitation, medical foods may include vitamin and mineral formulations fed through a feeding tube (referred to as enteral administration). A "dietary supplement" shall mean a product that is intended to supplement the human diet and is typically provided in the form of a pill, capsule, tablet or like formulation. By way of example, but not limitation, a dietary supplement may include one or more of the following ingredients: vitamins, minerals, herbs, botanicals; amino acids, dietary substances intended to supplement the diet by increasing total dietary intake, and concentrates, metabolites, constituents, extracts or combinations of any of the foregoing. Dietary supplements may also be incorporated into food, including, but not limited to, food bars, beverages, powders, cereals, cooked foods, food additives and candies; or other functional foods designed to promote health or to prevent or halt the progression of a degenerative disease associated with DUX4 expression or activity.

The subject compositions thus may be compounded with other physiologically acceptable materials that can be ingested including, but not limited to, foods. In addition or alternatively, the compositions for use as described herein may be administered orally in combination with (the separate) administration of food.

The compositions may be administered alone or in combination with other pharmaceutical or cosmetic agents and can be combined with a physiologically acceptable carrier thereof. In particular, the compounds described herein can be formulated as pharmaceutical or cosmetic compositions by formulation with additives such as pharmaceutically or physiologically acceptable excipients carriers, and vehicles. Suitable pharmaceutically or physiologically acceptable excipients, carriers and vehicles include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), and "Remington: The Science and Practice of Pharmacy," Lippincott Williams & Wilkins, Philadelphia, 20th edition (2003), $21^{st}$ edition (2005) and $22^{nd}$ edition (2012), incorporated herein by reference.

It is known that many molecules that inhibit CK1 can also inhibit p38. p38 mitogen-activated protein kinases are a class of mitogen-activated protein kinases (MAPKs) that are responsive to stress stimuli, such as cytokines, ultraviolet irradiation, heat shock, and osmotic shock, and are involved in cell differentiation, cytokine secretion, apoptosis and autophagy. Persistent activation of the p38 MAPK pathway in muscle satellite cells (muscle stem cells) due to ageing is known to impair muscle regeneration. In preferred embodiments, the CK1 inhibitor is also a p38 inhibitor.

Due to the homology between p38 and CK1, the invention also provides p38 inhibitors for use in the treatment of a disease or condition associated with DUX4 expression, wherein the p38 inhibitor reduces DUX4 expression. This is referred to hereinafter as a p38 inhibitor for use according to the invention. p38 inhibitors are known in the art. Except for exact molecular structure, terms and features of use according to the invention are as defined for the CK1 inhibitors for use according to the invention.

Examples of suitable p38 inhibitors are ARRY-797 (CHEMBL1088750, CAS: 1036404-17-7), LOSMAPIMOD (CHEMBL1088752, CAS: 585543-15-3), AZD-7624 (CHEMBL9960, CAS: 1095004-78-6), DORAMAPIMOD (CHEMBL103667), NEFLAMAPIMOD (CHEMBL119385, CAS: 209410-46-8), TAK-715 (CHEMBL363648, CAS: 303162-79-0), TALMAPIMOD (CHEMBL514201, CAS: 309913-83-5), PAMAPIMOD (CHEMBL1090089, CAS: 449811-01-2), VX-702 (CHEMBL1090090, CAS: 745833-23-2), PH-797804 (CHEMBL1088751, CAS: 586379-66-0), BMS-582949 (CHEMBL1230065, CAS: 623152-17-0), PF-03715455 (CHEMBL1938400, CAS: 1056164-52-3), DILMAPIMOD (CHEMBL2103838, CAS: 444606-18-2), SEMAPIMOD (CHEMBL2107779, CAS: 352513-83-8), RALIMETINIB (CHEMBL2364626, CAS: 862505-00-8), FX-005 (CHEMBL3545216, CAS: 2016822-86-7), ACUMAPIMOD (CHEMBL3545226, CAS: 836683-15-9), KC-706 (CHEMBL3545282, CAS: 896462-15-0), PG-760564 (CHEMBL3545398), RWJ-67657 (CHEMBL190333, CAS: 215303-72-3), RO-3201195 (CHEMBL203567, CAS: 249937-52-8), AMG-548 (CHEMBL585902, CAS: 864249-60-5), SD-0006 (CHEMBL1090173), SCIO-323

(CHEMBL1614702, CAS: 309913-51-7), R-1487 (CHEMBL1766582, CAS: 449808-64-4), AZD-6703 (CHEMBL2031465, CAS: 1083381-65-0), SC-80036 (CHEMBL3544930), GSK-610677 (CHEMBL3544968, CAS: 2016840-17-6), LY-3007113 (CHEMBL3544998), LEO-15520 (CHEMBL3545074), AVE-9940 (CHEMBL3545117, CAS: 1201685-00-8), PS-516895 (CHEMBL3545139), TA-5493 (CHEMBL3545201, CAS: 1073666-93-9), PEXMETINIB (ARRY614) (CHEMBL3545297, CAS: 945614-12-0), SB-85635 (CHEMBL3545384), and CK1 inhibitors.

Compositions for use according to the invention may be manufactured by processes well known in the art; e.g., by means of conventional mixing, dissolving, granulating, dragee-making, levigating, emulsifying, encapsulating, entrapping or lyophilizing processes, which may result in liposomal formulations, coacervates, oil-in-water emulsions, nanoparticulate/microparticulate powders, or any other shape or form. Compositions for use in accordance with the invention thus may be formulated in a conventional manner using one or more physiologically acceptable carriers comprising excipients and auxiliaries that facilitate processing of the active compounds into preparations which can be used pharmaceutically. Proper formulation is dependent on the route of administration chosen.

For injection, the CK1 inhibitors and compositions for use according to the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

Oral and parenteral administration may be used where the CK1 inhibitors and compositions for use are formulated by combining them with pharmaceutically acceptable carriers well known in the art, or by using them as a food additive. Such strategies enable the CK1 inhibitors and compositions for use according to the invention to be formulated as tablets, pills, dragées, capsules, liquids, gels, syrups, slurries, suspensions and the like, for oral ingestion by a subject to be treated.

Preparations or pharmacological preparations for oral use may be made with the use of a solid excipient, optionally grinding the resulting mixture, and processing the mixture of granules, after adding suitable auxiliaries, if desired, to obtain tablets or dragée cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as cross-linked polyvinyl pyrrolidone, agar, or alginic acid or a salt thereof such as sodium alginate. Additionally, coformulations may be made with uptake enhancers known in the art.

Dragée cores are provided with suitable coatings. For this purpose, concentrated sugar solutions may be used, which may optionally contain gum arabic, talc, PVP, carbopol gel, polyethylene glycol, and/or titanium dioxide, lacquer solution, and suitable organic solvents or solvent mixtures. Polymethacrylates can be used to provide pH-responsive release profiles so as to pass the stomach. Dyestuffs or pigments may be added to the tablets or dragée coatings for identification or to characterize different combinations of active CK1 inhibitor doses.

CK1 inhibitors and compositions which can be administered orally include push-fit capsules made of gelatin, as well as soft, sealed capsules made of gelatin and a plasticizer, such as glycerol or sorbitol. The push-fit capsules may contain the active ingredients in admixture with a filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the CK1 inhibitors and compositions for use according to the invention may be administered in the form of tablets or lozenges formulated in a conventional manner.

The CK1 inhibitors and compositions for use according to the invention may be formulated for parenteral administration by injection, e.g., by bolus injection or continuous infusion. In this way it is also possible to target a particular organ, tissue, tumor site, site of inflammation, etc.

Formulations for infection may be presented in unit dosage form, e.g., in ampoules or in multi-dose container, with an added preservative. The compositions may take such forms as suspensions, solutions or emulsions in oily or aqueous vehicles, and may contain formulatory agents such as suspending, stabilizing and/or dispersing agents. This formulation is preferred because it enables specific targeting of muscle tissue.

Compositions for parenteral administration include aqueous solutions of the compositions in water soluble form. Additionally, suspensions may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compositions to allow for the preparation of highly concentrated solutions.

Alternatively, one or more components of the composition may be in powder form for constitution with a suitable vehicle, e.g., sterile pyrogen-free water, before use.

The compositions for use according to the invention may also be formulated in rectal compositions such as suppositories or retention enemas, e.g., containing conventional suppository bases such as cocoa butter or other glycerides.

In addition to the formulations described previously, the CK1 inhibitors and compositions for use according to the invention may also be formulated as a depot preparation. Such long acting formulations may be administered by implantation (for example subcutaneously or intramuscularly) or by intramuscular injection. Thus, for example, they may be formulated with suitable polymeric or hydrophobic materials (for example as an emulsion in an acceptable oil), or as part of a solid or semi-solid implant that may or may not be auto-degrading in the body, or ion exchange resins, or one or more components of the composition can be formulated as sparingly soluble derivatives, for example, as a sparingly soluble salt. Examples of suitable polymeric materials are known to the person skilled in the art and include PLGA and polylactones such as polycaproic acid.

The compositions for use according to the invention also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

The compositions for use according to the invention may also be comprised in a transdermal patch. Preferred transdermal patches for use according to the invention are selected from single-layer drug-in-adhesive patch, or multi-layer drug-in-adhesive patch, or reservoir patch, or matrix patch, or vapour patch.

Compositions for use according to the invention include CK1 inhibitors and compositions wherein the active ingredients are contained in an amount effective to achieve their intended purposes. More specifically, a therapeutically effective amount means an amount of compound effective to prevent, stabilize, alleviate, revert, or ameliorate causes or symptoms of disease, or prolong the survival, mobility, or independence of the subject being treated. Determination of a therapeutically effective amount is within the capability of those skilled in the art, especially in light of the detailed disclosure provided herein. For any CK1 inhibitors and compositions used in the invention, the therapeutically effective amount or dose can be estimated initially from cell culture assays, for example as exemplified herein. Dosage may vary within this range depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics" Ch. 1 p. 1). The amount of CK1 inhibitors and compositions administered will, of course, be dependent on the subject being treated, on the subject's weight, the severity of the affliction, the manner of administration and the judgment of the prescribing physician.

A composition for use according to the invention may be supplied such that a CK1 inhibitor for use according to the invention and one or more of the other components as defined herein are in the same container, either in solution, in suspension, or in powder form. A composition for use according to the invention may also be provided with all components provided separately from one another, for example to be mixed with one another prior to administration, or for separate or sequential administration. Various packaging options are possible and known to the ones skilled in the art, depending, among others, on the route and mechanism of administration. In light of the methods of administration described above, the invention provides a casein kinase 1 inhibitor for use according to the invention, or a composition for use according to the invention, characterized in that it is administered orally, sublingually, intravascularly, intravenously, subcutaneously, or transdermally, or optionally by inhalation; preferably orally.

An "effective amount" of a CK1 inhibitor or composition is an amount which, when administered to a subject, is sufficient to reduce or eliminate either one or more symptoms of a disease, or to retard the progression of one or more symptoms of a disease, or to reduce the severity of one or more symptoms of a disease, or to suppress the manifestation of a disease, or to suppress the manifestation of adverse symptoms of a disease. An effective amount can be given in one or more administrations.

The "effective amount" of that may be combined with the carrier materials to produce a single dosage form will vary depending upon the host to which the active ingredient is administered and the particular mode of administration. The unit dosage chosen is usually fabricated and administered to provide a desired final concentration of the compound in the blood.

The effective amount (i.e. the effective total daily dose), preferably for adults, is herein defined as a total daily dose of about 0.01 to 2000 mg, or about 0.01 to 1000 mg, or about 0.01 to 500 mg, or about 5 to 1000 mg, or about 20 to 800 mg, or about 30 to 800 mg or about 30 to 700 mg, or about 20 to 700 mg or about 20 to 600 mg, or about 30 to 600 mg, or about 30 to 500 mg, about 30 to 450 mg or about 30 to 400 mg, or about 30 to 350 mg or about 30 to 300 mg or about 50 to 600 mg, or about 50 to 500 mg, or about 50 to 450 mg, or about 50 to 400 mg, or about 50 to 300 mg, or about 50 to 250 mg, or about 100 to 250 mg or about 150 to 250 mg. In the most preferred embodiment, the effective amount is about 200 mg. In preferred embodiments, the invention provides a casein kinase 1 inhibitor for use according to the invention, or a composition for use according to the invention, characterized in that it is administered to a subject in an amount ranging from 0.1 to 1500 mg/day, preferably from 0.1 to 1000 mg/day, more preferably from 0.1 to 400 mg/day, still more preferably from 0.25 to 150 mg/day, such as about 100 mg/day.

Alternatively, the effective amount of the compound, preferably for adults, preferably is administered per kg body weight. The total daily dose, preferably for adults, is therefore about 0.05 to about 40 mg/kg, about 0.1 to about 20 mg/kg, about 0.2 mg/kg to about 15 mg/kg, or about 0.3 mg/kg to about 15 mg/kg or about 0.4 mg/kg to about 15 mg/kg or about 0.5 mg/kg to about 14 mg/kg or about 0.3 mg/kg to about 14 mg/kg or about 0.3 mg/kg to about 13 mg/kg or about 0.5 mg/kg to about 13 mg/kg or about 0.5 mg/kg to about 11 mg/kg.

The total daily dose for children is preferably at most 200 mg. More preferably the total daily dose is about 0.1 to 200 mg, about 1 to 200 mg, about 5 to 200 mg about 20 to 200 mg about 40 to 200 mg, or about 50 to 200 mg. Preferably, the total daily dose for children is about 0.1 to 150 mg, about 1 to 150 mg, about 5 to 150 mg about 10 to 150 mg about 40 to 150 mg, or about 50 to 150 mg. More preferably, the total daily dose is about 5 to 100 mg, about 10 to 100 mg, about 20 to 100 mg about 30 to 100 mg about 40 to 100 mg, or about 50 to 100 mg. Even more preferably, the total daily dose is about 5 to 75 mg, about 10 to 75 mg, about 20 to 75 mg about 30 to 75 mg about 40 to 75 mg, or about 50 to 75 mg.

Alternative examples of dosages which can be used are an effective amount of the compounds for use according to the invention within the dosage range of about 0.1 µg/kg to about 300 mg/kg, or within about 1.0 µg/kg to about 40 mg/kg body weight, or within about 1.0 µg/kg to about 20 mg/kg body weight, or within about 1.0 µg/kg to about 10 mg/kg body weight, or within about 10.0 µg/kg to about 10 mg/kg body weight, or within about 100 µg/kg to about 10 mg/kg body weight, or within about 1.0 mg/kg to about 10 mg/kg body weight, or within about 10 mg/kg to about 100 mg/kg body weight, or within about 50 mg/kg to about 150 mg/kg body weight, or within about 100 mg/kg to about 200 mg/kg body weight, or within about 150 mg/kg to about 250 mg/kg body weight, or within about 200 mg/kg to about 300 mg/kg body weight, or within about 250 mg/kg to about 300 mg/kg body weight. Other dosages which can be used are about 0.01 mg/kg body weight, about 0.1 mg/kg body weight, about 1 mg/kg body weight, about 10 mg/kg body weight, about 20 mg/kg body weight, about 30 mg/kg body weight, about 40 mg/kg body weight, about 50 mg/kg body weight, about 75 mg/kg body weight, about 100 mg/kg body weight, about 125 mg/kg body weight, about 150 mg/kg body weight, about 175 mg/kg body weight, about 200 mg/kg body weight, about 225 mg/kg body weight, about 250 mg/kg body weight, about 275 mg/kg body weight, or about 300 mg/kg body weight.

Compounds or compositions for use according to the present invention may be administered in a single daily dose, or the total daily dosage may be administered in divided dosage of two, three or four times daily.

In a preferred embodiment of the invention, "subject", "individual", or "patient" is understood to be an individual organism, preferably a vertebrate, more preferably a mammal, even more preferably a primate and most preferably a human.

In a further preferred embodiment of the invention, the human is an adult, e.g. a person that is 18 years or older. In addition, it is herein understood that the average weight of an adult person is 62 kg, although the average weight is known to vary between countries. In another embodiment of the invention the average weight of an adult person is therefore between about 50-90 kg. It is herein understood that the effective dose as defined herein is not confined to subjects having an average weight. Preferably, the subject has a BMI (Body Mass Index) between 18.0 to 40.0 kg/m$^2$, and more preferably a BMI between 18.0 to 30.0 kg/m$^2$.

Alternatively, the subject to be treated is a child, e.g. a person that is 17 years or younger. In addition, the subject to be treated may be a person between birth and puberty or between puberty and adulthood. It is herein understood that puberty starts for females at the age of 10-11 years and for males at the age of 11-12 year. Furthermore, the subject to be treated may be a neonate (first 28 days after birth), an infant (0-1 year), a toddler (1-3 years), a preschooler (3-5 years); a school-aged child (5-12 years) or an adolescent (13-18 years).

To maintain an effective range during treatment, the CK1 inhibitor or composition may be administered once a day, or once every two, three, four, or five days. However preferably, the compound may be administered at least once a day. Hence in a preferred embodiment, the invention pertains to a casein kinase 1 inhibitor for use according to the invention, or a composition for use according to the invention, characterized in that it is administered to a subject 4, 3, 2, or 1 times per day or less, preferably 1 time per day. The total daily dose may be administered as a single daily dose. Alternatively, the compound is administered at least twice daily. Hence, the compound as defined herein may be administered once, twice, three, four or five times a day. As such, the total daily dose may be divided over the several doses (units) resulting in the administration of the total daily dose as defined herein. In a preferred embodiment, the compound is administered twice daily. It is further understood that the terms "twice daily", "bid" and "bis in die" can be used interchangeable herein.

In a preferred embodiment, the total daily dose is divided over several doses per day. These separate doses may differ in amount. For example for each total daily dose, the first dose may have a larger amount of the compound than the second dose or vice versa. However preferably, the compound is administered in similar or equal doses. Therefore in a most preferred embodiment, the compound is administered twice daily in two similar or equal doses.

In a further preferred embodiment of the invention, the total daily dose of the compound as defined herein above is administered in at least two separate doses. The interval between the administration of the at least two separate doses is at least about 0.5, 1, 2, 3, 4, 5, 6, 7, 8, 9, 10, 11 or 12 hours, preferably the interval between the at least two separate doses is at least about 4, 5, 6, 7, 8, 9, 10, 11 or 12 hours and more preferably the interval between the at least two separate doses is at least about 8, 9, 10, 11 or 12 hours.

Use

In one aspect of the invention, the use is provided of either a CK1 inhibitor according to the invention, or of a composition according to the invention. Said use is for the treatment of a disease or condition associated with DUX4 expression of a subject in need thereof, and comprises administration to the subject of an effective dose of a CK1 inhibitor or composition according to the invention, wherein the CK1 inhibitor or composition are as defined earlier herein.

In one embodiment of this aspect, the use is provided of either a CK1 inhibitor according to the invention, or of a composition according to the invention. Said use is for the treatment of muscular dystrophy or cancer in a subject in need thereof, and comprises administration to the subject of an effective dose of a CK1 inhibitor or composition according to the invention, wherein the CK1 inhibitor or composition are as defined earlier herein. Further features and definitions are preferably as defined elsewhere herein, particularly for diseases or conditions to be treated.

Method

One aspect of the invention provides an in vivo, in vitro, or ex vivo method for reducing DUX4 expression, the method comprising the step of contacting a cell with a CK1 inhibitor as defined earlier herein, or with a composition as defined earlier herein. Preferably, said method is for treating a disease or condition associated with DUX4 expression, such as a muscular dystrophy or cancer, most preferably said disease or condition is facioscapulohumeral muscular dystrophy (FSHD). The method preferably comprises use as defined earlier herein. Preferred methods comprise contacting a cell with a CK1 inhibitor composition as defined earlier herein. In the context of the invention, contacting a cell with a CK1 inhibitor or a composition can comprise adding such a CK1 inhibitor or composition to a medium in which a cell is cultured. Contacting a cell with a CK1 inhibitor or a composition can also comprise adding such a CK1 inhibitor or composition to a medium, buffer, or solution in which a cell is suspended, or which covers a cell. Other preferred methods of contacting a cell comprise injecting a cell with a CK1 inhibitor or composition, or exposing a cell to a material comprising a CK1 inhibitor or composition according to the invention. Further methods for administration are defined elsewhere herein. Preferred cells are cells known to express DUX4, cells suspected of expressing DUX4, or cells known to be affected by a disease or condition as defined earlier herein.

In one embodiment of this aspect, the method is an in vitro method. In a further embodiment of this aspect, the method is an ex vivo method. In a further embodiment of this aspect, the method is an in vivo method. In a preferred embodiment of this aspect, the method is an in vitro or an ex vivo method.

Within the embodiments of this aspect, the cell may be a cell from a sample obtained from a subject. Such a sample may be a sample that has been previously obtained from a subject. Within the embodiments of this aspect, samples may have been previously obtained from a human subject. Within the embodiments of this aspect, samples may have been obtained from a non-human subject. In a preferred embodiment of this aspect, obtaining the sample is not part of the method according to the invention.

In preferred embodiments, the method according to the invention is a method for reducing DUX4 expression in a subject in need thereof, the method comprising the step of administering an effective amount of a CK1 inhibitor as defined earlier herein, or a composition as defined earlier herein. In more preferred embodiments, the method is for the treatment of a disease or condition associated with DUX4 expression, preferably a muscular dystrophy or cancer, most preferably said disease or condition is facioscapulohumeral muscular dystrophy (FSHD). Further features and definitions are preferably as defined elsewhere herein.

General Definitions

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a combination or a composition as defined herein may comprise additional component(s) than the ones specifically identified, said additional component(s) not altering the unique characteristic of the invention. In addition, reference to an element by the indefinite article "a" or "an" does not exclude the possibility that more than one of the element is present, unless the context clearly requires that there be one and only one of the elements. The indefinite article "a" or "an" thus usually means "at least one".

When a structural formula or chemical name is understood by the skilled person to have chiral centers, yet no chirality is indicated, for each chiral center individual reference is made to all three of either the racemic mixture, the pure R enantiomer, and the pure S enantiomer.

Whenever a parameter of a substance is discussed in the context of this invention, it is assumed that unless otherwise specified, the parameter is determined, measured, or manifested under physiological conditions. Physiological conditions are known to a person skilled in the art, and comprise aqueous solvent systems, atmospheric pressure, pH-values between 6 and 8, a temperature ranging from room temperature to about 37° C. (from about 20° C. to about 40° C.), and a suitable concentration of buffer salts or other components.

The use of a substance as a medicament as described in this document can also be interpreted as the use of said substance in the manufacture of a medicament. Similarly, whenever a substance is used for treatment or as a medicament, it can also be used for the manufacture of a medicament for treatment. Products for use as a medicament described herein can be used in methods of treatments, wherein such methods of treatment comprise the administration of the product for use. CK1 inhibitors or compositions according to this invention are preferably for use in methods or uses according to this invention.

Throughout this application, expression is considered to be the transcription of a gene into functional mRNA, leading to a polypeptide such as an enzyme or transcription factor or for example DUX4 polypeptide. A polypeptide can assert an effect or have an activity. In this context, increased or decreased expression of a polypeptide can be considered an increased or decreased level of mRNA encoding said polypeptide, an increased or decreased level or amount of polypeptide molecules, or an increased or decreased total activity of said polypeptide molecules. Preferably, an increased or decreased expression of a polypeptide results in an increased or decreased activity of said polypeptide, respectively, which can be caused by increased or decreased levels or amounts of polypeptide molecules. More preferably, a reduction of DUX4 expression is a reduction of transcription of a DUX4 gene, destabilisation or degradation of DUX4 mRNA, reduction of the amount of DUX4 polypeptide molecules, reduction of DUX4 polypeptides molecule activity, destabilisation or degradation of DUX4 polypeptide, or combinations thereof. A destabilized mRNA leads to lower expression of its encoded polypeptide, possibly it cannot lead to such expression. A degraded mRNA is destroyed and cannot lead to expression of its encoded polypeptide. A destabilized polypeptide asserts less of an effect or has lower activity than the same polypeptide that has not been destabilized, possibly it asserts no effect or has no activity. A destabilized polypeptide can be denatured or misfolded. A degraded polypeptide is destroyed and does not assert an effect or have an activity.

In the context of this invention, a decrease or increase of a parameter to be assessed means a change of at least 5% of the value corresponding to that parameter. More preferably, a decrease or increase of the value means a change of at least 10%, even more preferably at least 20%, at least 30%, at least 40%, at least 50%, at least 70%, at least 90%, or 100%. In this latter case, it can be the case that there is no longer a detectable value associated with the parameter.

The word "about" or "approximately" when used in association with a numerical value (e.g. about 10) preferably means that the value may be the given value (of 10) more or less 1% of the value.

Each embodiment as identified herein may be combined together unless otherwise indicated. The invention has been described above with reference to a number of embodiments. A skilled person could envision trivial variations for some elements of the embodiments. These are included in the scope of protection as defined in the appended claims. All patent and literature references cited are hereby incorporated by reference in their entirety.

SHORT DESCRIPTION OF DRAWINGS

FIG. 1—(A): Illustration of a DUX4 immunocytochemistry staining in FSHD myotubes from 2 different donors after 3 days of differentiation. DUX4-positive nuclei clusters are clearly stained, while DUX4-negative nuclei are not stained. The histograms show the intensity of the immunofluorescent signals (increasing intensity on the X-axis) after staining with the DUX4 and secondary antibody (top) or the secondary antibody alone (bottom); the arrows on top show the background signal (leftward arrow) or specific DUX4 signal (rightward arrow); (B): Illustration of a DUX4-stained FSHD myotube after 3 days of differentiation. The dotted pattern results from the applied filter settings to deplete the background from the secondary antibody control. Note that the threshold settings prohibit detection of the weaker DUX4 signal in the nuclei more distant from the sentinel nucleus.

Figure 2:
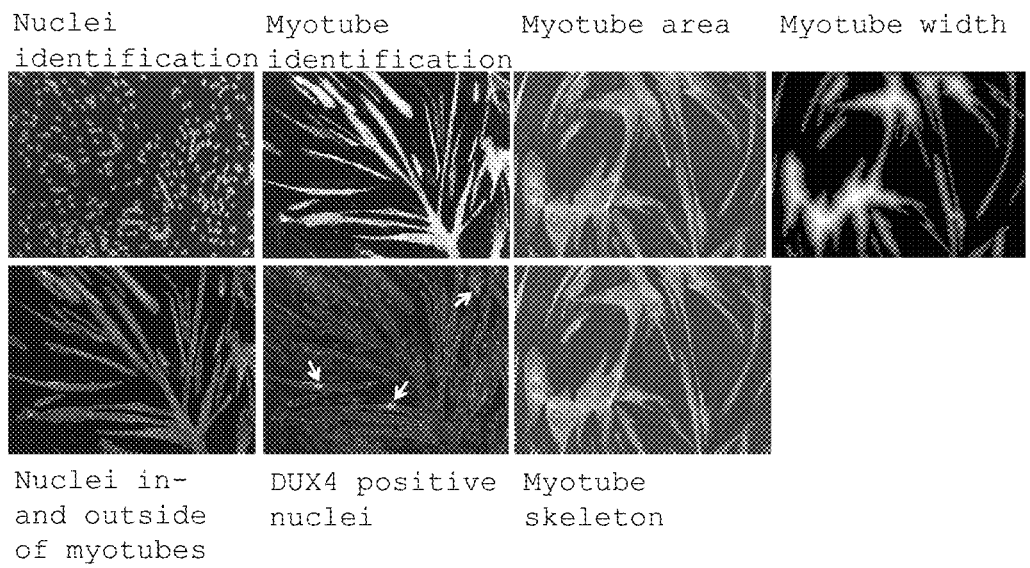

FIG. 2—Script-based image analysis includes nuclei identification, myotube identification, detection of nuclei inside or outside myotube borders (used to calculate fusion index), DUX4 positive nuclei and clusters, myotube area, myotube width, and myotube skeleton length.

Figure 3:
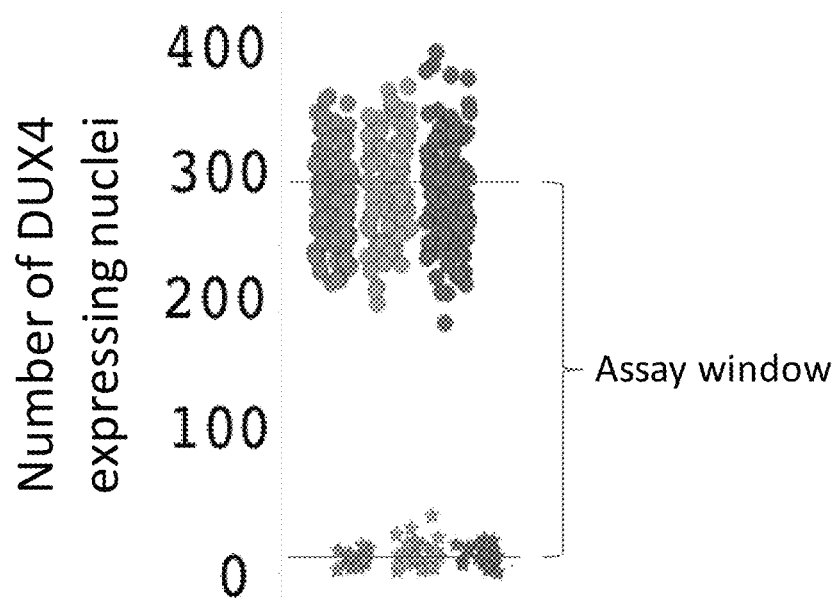

FIG. 3—Validation of the primary screening assay format in 384-well format. Three independent experiments are shown, illustrating the assay window obtained using script-based quantification of the number of DUX4-expressing nuclei in differentiating primary myotubes after 3 days in differentiation medium. The assay window is defined by the DUX4 signal and the background signal of the secondary antibody (representing the signal in total absence of DUX4).

Figure 4:
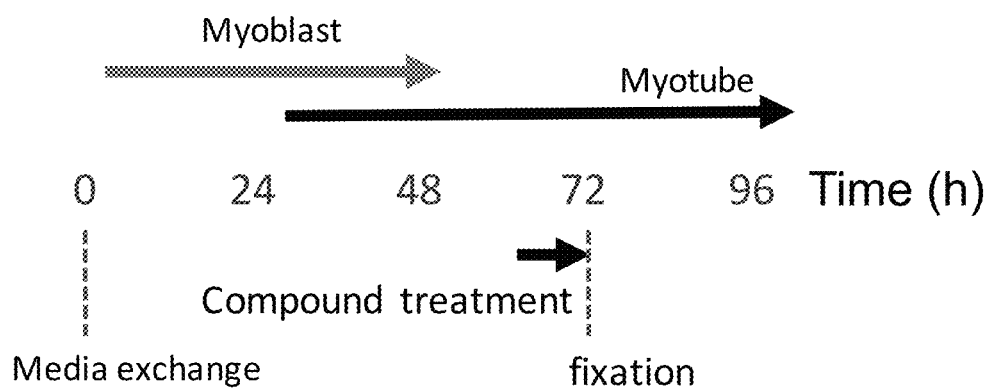
Figure 4:
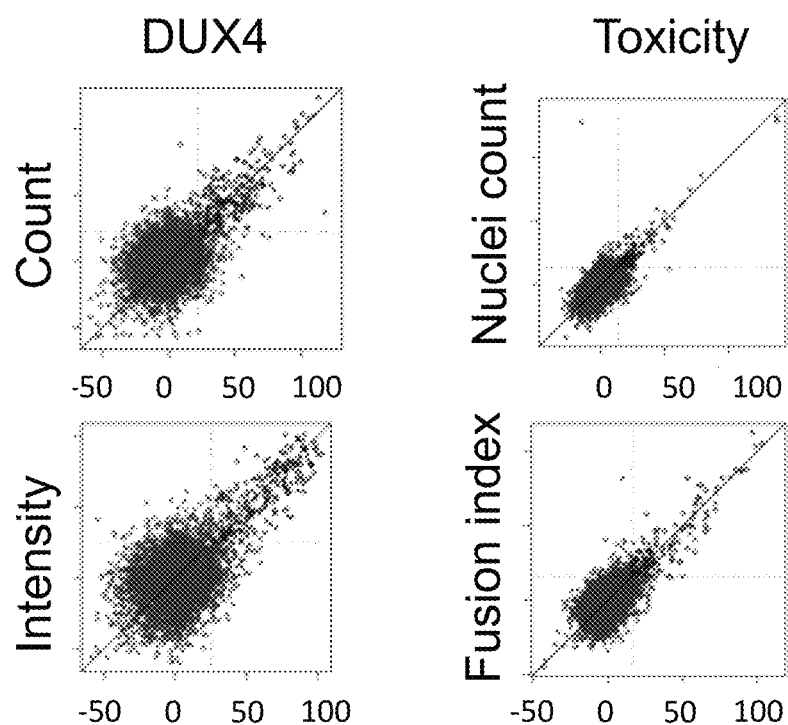

FIG. 4—(A): Schematic representation of the screening assay protocol. Myoblasts were seeded at day −1 and medium was changed to differentiation medium at day zero. Cells were allowed to differentiate for 3 days. Compounds were added 15 h prior to fixation. (B): Correlation of duplicated results from primary screening of an annotated compound library using 2 different readouts for DUX4 expression (Number of DUX4-positive nuclei and DUX4 intensity) and 2 different readouts to monitor potential toxicity (fusion index, nuclei count). Hit calling thresholds (high stringency) are indicated by a dashed line, and the upper right quadrants contain the hit compounds for the different readouts. Axes of the scatter plots are symmetrical.

Figure 5:
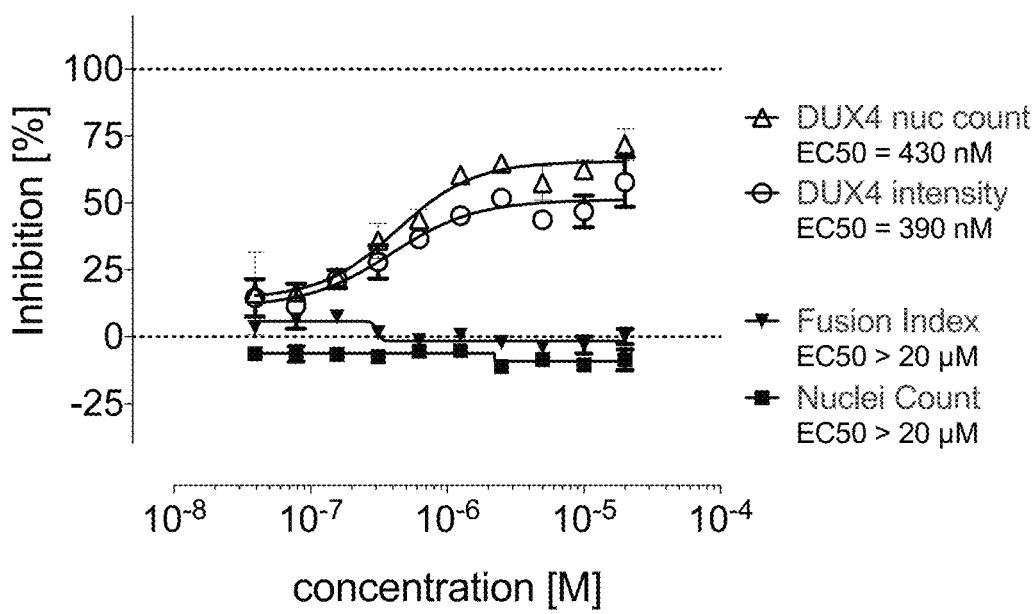
Figure 5:
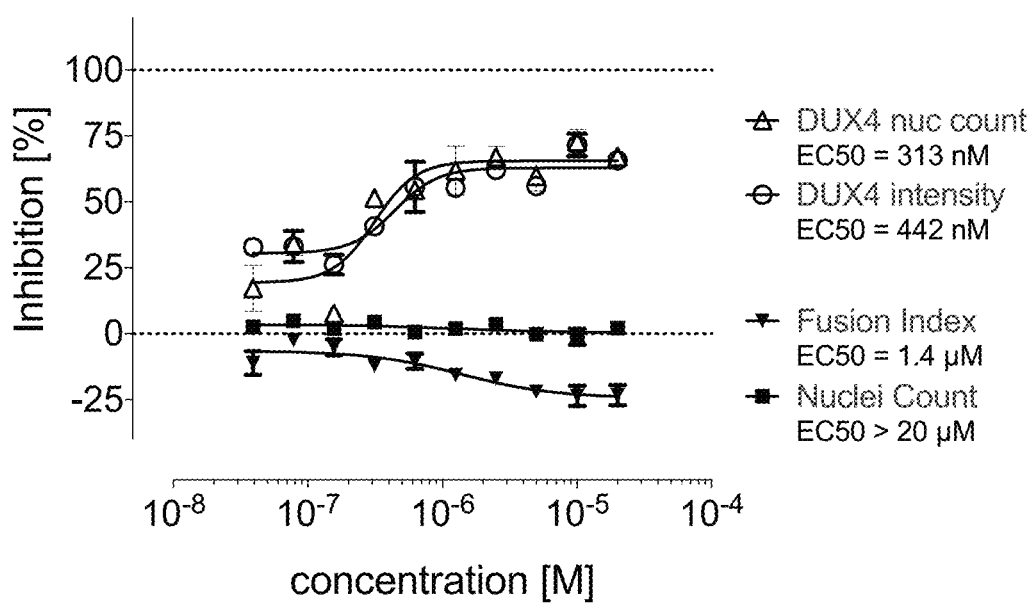

FIG. 5—Concentration-response curves for various CK1 inhibitors for the different readouts. The DUX4 nuclei count, DUX4 intensity, fusion index, and total nucleus count were measured after 15 hour of compound exposure. (A): results for PF-670462; (B): results for PF-5006739; (C): results for compound C; (D): results for compound D; (E): results for compound E; (F): results for compound F; (G): results for compound G; Structural formulae are shown in example 5.

FIG. 6—(A): Schematic representation of the assay protocol. Myoblasts were seeded at day −1 and medium was changed to differentiation medium at day zero. Cells were allowed to differentiate for 3 days. Compounds were added for 15 h or 72 h prior to fixation. For the 15 h treatment, compounds are administered when differentiation already progressed significantly. In case of 72 h treatment, compounds were incubated during the full differentiation phase. The other panels show concentration-response curves for a BET inhibitors (B, C) or for beta2 adrenoreceptor agonists (D, E, F, G, H, I) for the different readouts. DUX4 nuclei count, DUX4 intensity, fusion index, and total nuclei count were assessed after 15 h or after 72 h of treatment. (B, C): (+)JQ1; (D, E): formoterol; (F, G): salbutamol; (H, I): salmeterol; (J): micrographs of myotubes after 72 hours in differentiation medium while exposed to the a beta2 adrenoreceptor agonist (formoterol); (K, L): results for both 15 hour and 72 hour exposure to a CK1 inhibitor (PF-670462).

EXAMPLES

Example 1—Primary FSHD Muscle Cells Express DUX4 in a Small Fraction of Myonuclei The inventors succeeded in establishing a sensitive DUX4 detection method in primary myotubes and used this to build a high-content assay for quantitative assessment of endogenous DUX4 expression. The method was developed into a validated phenotypic screening platform for automated detection and quantification of endogenous DUX4 expression. Mechanisms underlying DUX4 repression may involve many interacting proteins, favouring such a phenotypic approach. Furthermore, it is pathway/target independent (and thus not hypothesis-driven) and provides additional information on cell toxicity or interference with muscle differentiation.

Significant differences in the levels of DUX4 expression between cells obtained from different donors have been reported. Therefore, muscle cell lines derived from different donors were thoroughly characterised and an optimal cell line was selected for primary screening. MyoD staining of myoblasts confirmed solid myogenicity of all cell lines (Rudnicki et al., 1993; cell 75(7):1351-9). After optimisation of parameters, a DUX4 detection procedure was established that could be applied in a screening assay which resulted in the expected DUX4 pattern in FSHD cells, but not in myotubes from healthy donors. As shown in FIG. 1, this included a nuclear DUX4 localization, with only few positive cells, and an intensity gradient through DUX4-positive nuclear clusters, as also described by Rickard et al., (2015, DOI: 10.1093/hmg/ddv315).

Example 2—Screening Assay to Identify DUX4 Repression

A quantitative assay readout was developed based on script-based image analysis. Cells were stained according to example 1, also using DAPI to detect myonuclei and an antibody against myosin heavy chain (MHC) to visualize the formation of myotubes. To analyse the images, an automated script was developed, enabling the detection of nuclei, myotube borders and DUX4 signals, with the script also detecting artefacts to reduce false positive signals. The script enabled multiple validated readouts including the number of DUX4 positive nuclei and nuclei clusters, the fusion index, myotube area, myotube width and myotube skeleton length (see FIG. 2). Additionally, the total nuclei count was included as a measure of cell loss or compound toxicity. The script was validated by evaluating endogenous DUX4 expression in the primary myotubes, and results were in line with literature values, with the number of DUX4 expressing nuclei being <0.5%.

The assay has been further matured to make it suitable for screening purposes. The assay quality was dependent on the donor cell line. The number of DUX4 positive nuclei was characteristic for each donor cell line, and was consistent between experiments. The best performing cell lines in terms of number of DUX4 expressing nuclei, reproducibility and Z-factor have been selected for miniaturization of the assay to a 384-well format, thus allowing for automated screening of large compound libraries. A cell line with 2 D4Z4 repeats was selected for the primary screening, while a cell line with 6 D4Z4 repeats was selected for later validation. The primary screening assay had a Z-factor of 0.6, which represents an excellent assay (Zhang et al., 1999, doi:10.1177/108705719900400206; see FIG. 3).

A compound library containing approximately 5000 annotated compounds was screened in the high-content assay. For this purpose, primary myoblasts were seeded in 384 well plates after which the growth medium was replaced with differentiation medium. After 3 days of differentiation, cells were treated with library compounds (in duplicate on different screening plates) for 15 h, after which they were fixed and stained with antibodies against DUX4, antibodies against myosin heavy chain (MHC), and with DAPI (4′,6-diamidino-2-phenylindole). Script-based analysis provided readouts for DUX4 expression (count of DUX4-positive nuclei or DUX4 intensity) and for potential toxicity (fusion index and nuclei count). Results are shown in FIG. 4. The majority of the approximately 200 hits was confirmed in an experiment using the same assay and 5 replicates. These compounds were selected for further concentration-response profiling.

Half of these hits were validated using RT-PCR. Based on mRNA expression of DUX4 and the downstream target genes Trim43 & ZScan4, using housekeeping genes hGUSB, GAPDH, hRPL27 as a reference, a very good correlation between DUX4 repression in the immunocytochemistry assay (protein level) and the RT-PCR assay (mRNA level) was observed. This suggests that the vast majority of the hits have an upstream mode of action, i.e. they act by inhibiting the expression of DUX4 (as opposed to accelerating degradation of DUX4).

RT-PCR was performed as described by Lemmers et al., (2010, DOI: 10.1126/science.1189044) using oligonucleotides ordered from Applied Biosystems (Foster City, USA), possibly as part of assay kits (for hGAPDH (app): AssayID Hs02758991_g1; for hTRIM43(app): Assay ID Hs00299174_m1; for hMYH2_tv1-2(app): AssayID Hs00430042_m1). Other oligonucleotides are shown in table 1.

TABLE 1 primers and probes for use in PCR

| Name | Sequence | SEQ ID NO: |
|---|---|---|
| hDUX4 forward | CCCGGCTGACGTGCAA | 1 |
| hDUX4 reverse | AGCCAGAATTTCACGGAAGAAC | 2 |
| hDUX4 probe | AGCTCGCTGGCCTCTCTGTGCC | 3 |
| hGUSB forward | TTCCCTCCAGCTTCAATGACA | 4 |
| hGUSB reverse | CCACACCCAGCCGACAA | 5 |
| hGUSB probe | AGGACTGGCGTCTGCGGCA | 6 |
| hRPL27 forward | TGTCCTGGCTGGACGCTACT | 7 |
| hRPL27 reverse | GAGGTGCCATCATCAATGTTCTT | 8 |
| hRPL27 probe | CGGACGCAAAGCTGTCATCGT | 9 |
| hZSCAN4 forward | AGGCAGGAATTGCAAAGACTTT | 10 |
| hZSCAN4 reverse | AATTTCATCCTTGCTGTGCTTTT | 11 |
| hZSCAN4 probe | TAGGATCTTTCACTCATGGCTGCAACCA | 12 |
| hMYOG forward | GCTCACGGCTGACCCTACA | 13 |
| hMYOG reverse | CACTGTGATGCTGTCCACGAT | 14 |
| hMYOG probe | CCCACAACCTGCACTCCCTCACCT | 15 |

Example 3—CK1 Inhibitors Act as DUX4 Repressors

The validated assay was used for screening an annotated compound library containing approximately 5000 compounds, to identify novel mechanisms of action for DUX4 repression. This library contained compounds with annotated pharmacology, not only entailing the primary pharmacology of the compounds but also potential known polypharmacology. The primary screening achieved multiple hits, identifying compounds that reduced the number of DUX4 positive nuclei. Hits were further profiled by establishing concentration-response curves. By applying a bioinformatics approach on the screening and profiling dataset, the inventors surprisingly discovered that compounds with a CK1 annotation were significantly enriched in the phenotypically active compound population, i.e. in the group of compounds inducing a repression of DUX4. Interestingly, none of the original compounds with a CK1 annotation had CK1 as its primary pharmacological target, each having other high potency targets from other protein families. Thus the bioinformatics analysis was essential in identifying the association between CK1 and DUX4 repression.

Profiled compounds were annotated as being phenotypically active when they showed a concentration-dependent effect on DUX4 (inhibition or activation). Of these, compounds which showed inhibition of the fusion index or of the total number of nuclei by more than 10% were excluded unless the effect on these readouts was at least 5-fold less potent than the effect on DUX4. As such, from the 4790 unique compounds, 188 compounds were classified as being phenotypically active, 162 of which were DUX4 inhibitors.

For the phenotypically active compounds, the original target annotations were complemented with additional information that is publically available (literature, patent applications, supplier databases, etc.). All human proteins, and non-human orthologues where a mapping to the human proteome can be established, were considered. Each of the 4790 compounds was then evaluated against these target annotations, classifying the target as being active or inactive for a given compound. For the phenotypically active compounds, the annotated targets were classified as being active if the compound's potency on the target was ≤10 times the phenotypic potency, otherwise the target was classified as inactive. This analysis revealed that approximately 201 targets were associated with phenotypic activity at a False Discovery Rate of 0.05. An enrichment of compounds annotated as CK1 inhibitors was detected in the group of phenotypically active compounds.

Example 4—CK1 Isoforms are Expressed in FSHD Primary Muscle Cells

To confirm target expression in both healthy and FSHD muscle cells, an RNA sequencing approach was followed to determine the expression of the different CK1 isoforms in primary myotubes from 4 different FSHD donors and from 4 different healthy donors. The results show expression of all CK1 isoforms, both in FSHD and in healthy muscle cells. The highest expression is of CK1 α, CK1 δ and CK1 ε (see table 2).

TABLE 2 expression of casein kinase 1 isoforms in 4 healthy primary cell lines, and in 4 FSHD primary cell lines as determined by RNA sequencing of differentiated myotubes

| | CSNK1A1 | CSNK1D | CSNK1E | CSNK1G1 | CSNK1G2 | CSNK1G3 |
|---|---|---|---|---|---|---|
| FSHD | 134 | 159.1 | 160.1 | 49.9 | 81.8 | 37.9 |
| FSHD | 122.5 | 138.4 | 136.8 | 4.2 | 79.1 | 32.7 |

TABLE 2-continued expression of casein kinase 1 isoforms in 4 healthy primary cell lines, and in 4
FSHD primary cell lines as determined by RNA sequencing of differentiated myotubes

|  | CSNK1A1 | CSNK1D | CSNK1E | CSNK1G1 | CSNK1G2 | CSNK1G3 |
|---|---|---|---|---|---|---|
| FSHD | 176.7 | 170.6 | 120.5 | 69.8 | 65.8 | 41.3 |
| FSHD | 118.2 | 134 | 105.6 | 41.8 | 63.5 | 38.1 |
| Healthy | 138.9 | 168.5 | 188 | 45.8 | 75.9 | 35.8 |
| Healthy | 143.3 | 174.1 | 200.7 | 49.6 | 81.8 | 36.3 |
| Healthy | 139.2 | 192.8 | 176.1 | 51.9 | 71.4 | 33.2 |
| Healthy | 119.1 | 132.4 | 122.4 | 40.6 | 65.9 | 40.1 |

Example 5—Inhibition of CK1 Represses DUX4

The DUX4 repression of CK1 inhibitors was assayed following the protocol of Example 2, illustrated in FIG. 4A. Tanmble 3 shows the structures of the CK1 inhibitors that are used in FIG. 5. Compounds were incubated with primary FSHD cells for 15 hours, as indicated by the arrow in FIG. 4A. Results are shown in FIG. 5, while table 3 shows half maximal effective concentrations ($EC_{50}$) values. Table 3 also shows determined $IC_{50}$ values in nM for CK1α, CK1δ, CK1ε, and p38α, denoted as CK1 a, d, e, and p38a, respectively.

TABLE 3

Examplary CK1 inhibitors for use according to the invention, along with half maximal effective concentrations ($EC_{50}$)

PF-670462
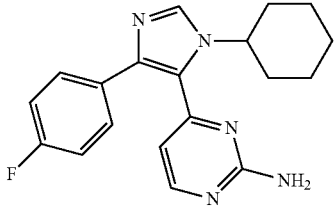
($EC_{50}$ 0.43 μM)
CK1 a: 320; d: 29.1; e: 99.8; p38a: 32.4

PF-5006739
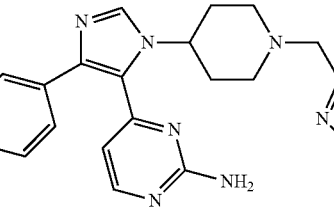
($EC_{50}$ 0.31 μM)
CK1 a: 123; d: 19.8; e: 26.8; p38a: 74.3

Compound A
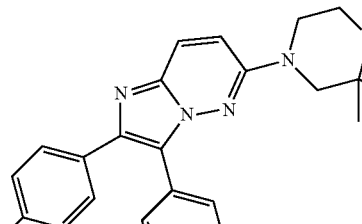
($EC_{50}$ <0.04-0.05 μM)
CK1 a: 29.5; d: 18.5; e: 12.4; p38a: 13.2

TABLE 3-continued

Examplary CK1 inhibitors for use according to the invention, along with half maximal effective concentrations ($EC_{50}$)

Compound B
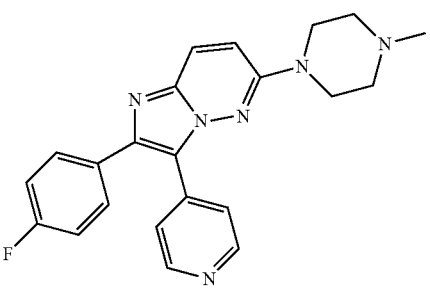
($EC_{50}$ 2 μM)

Compound C
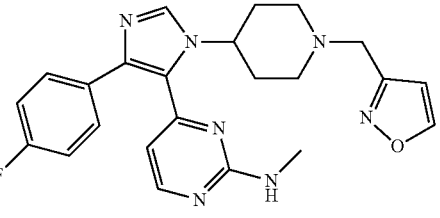
($EC_{50}$ 1.1-1.4 μM)

Compound D
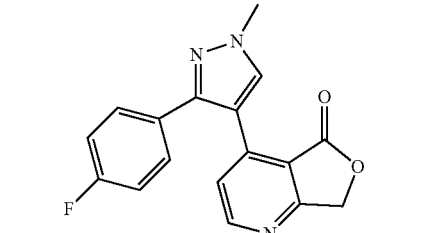
($EC_{50}$ 1.4 μM)
CK1 a: 644; d: 33.1; e: 51.6; p38a: 569

Compound E
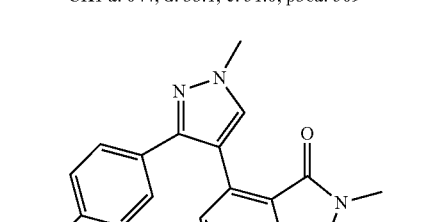
($EC_{50}$ 1.9-3.1 μM)
CK1 a: 592; d: 30.7; e: 83.6; p38a: 1110

TABLE 3-continued

Examplary CK1 inhibitors for use according to the invention, along with half maximal effective concentrations (EC$_{50}$)

Compound F

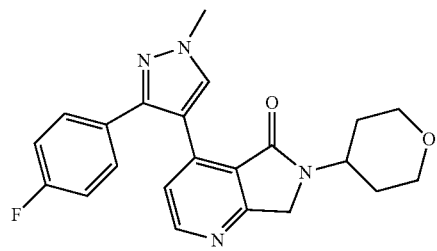

(EC$_{50}$ 1.5-2.6 µM)
CK1 a: 561; d: 18; e: 72.4; p38a: 677

Compound G

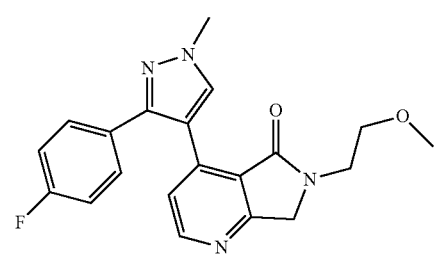

(EC$_{50}$ 1.7-4.5 µM)
CK1 a: 2590; d: 41.8; e: 92.1; p38a: 712

Compound H

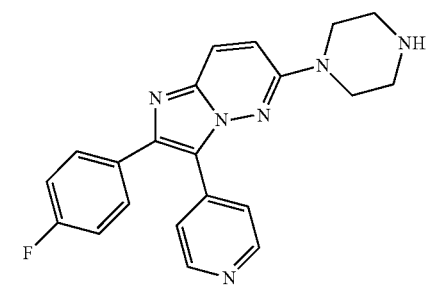

(EC$_{50}$ 0.01-0.046 µM)
CK1 a: 22; d: 16.5; e: 9.41; p38a: 14.8

Compound I

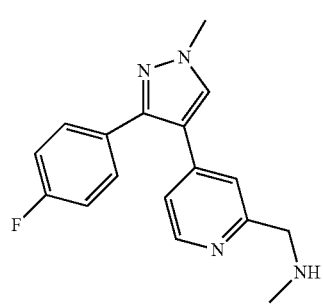

(EC$_{50}$ 3.1-5.5 µM)
CK1 a: 1760; d: 57.7; e: 89; p38a: 3070

TABLE 3-continued

Examplary CK1 inhibitors for use according to the invention, along with half maximal effective concentrations (EC$_{50}$)

Compound J

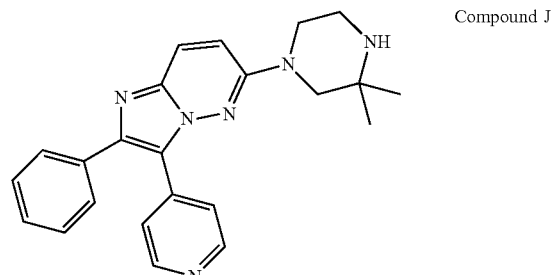

Compound K

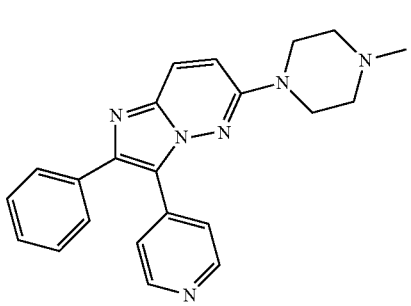 [SMILES: CN1CCN(c2ccc3nc(-c4ccccc4)c(-c4ccncc4)n3n2)CC1]

Compound L

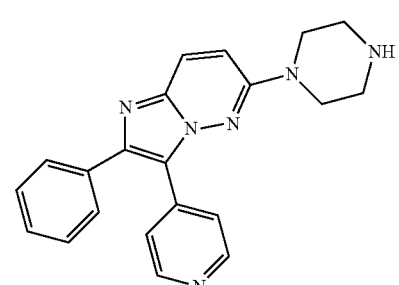

Compound M

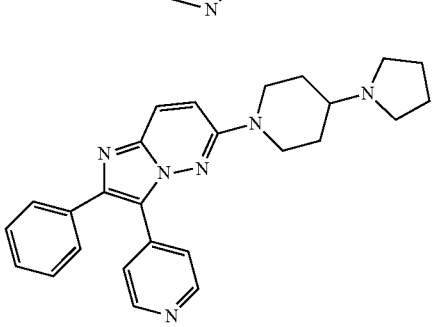

Compound N

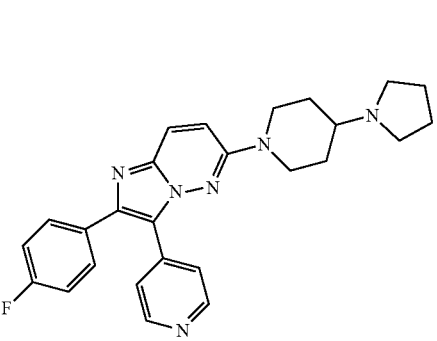 [SMILES: Fc1ccc(-c2nc3ccc(N4CCC(N5CCCC5)CC4)nn3c2-c2ccncc2)cc1]

TABLE 3-continued

Examplary CK1 inhibitors for use according to the invention, along with half maximal effective concentrations (EC$_{50}$)

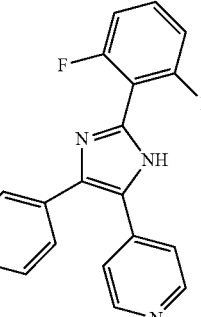

Compound O (EC$_{50}$ 0.71 µM)

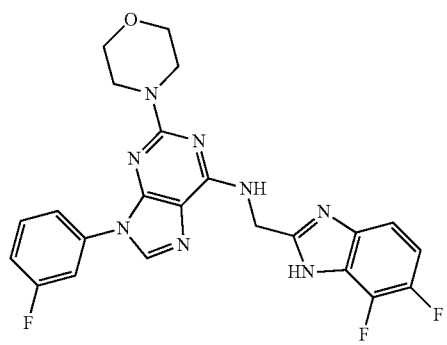

SR-3029

(EC$_{50}$ 0.05-0.12 µM)
CK1 α: 1000; δ: 346; ε: 38; p38a: 1000

Several of these compounds were also tested in vivo in a mouse model. The model was based on human FSHD-affected myoblasts engrafted onto a mouse thigh muscle. These human FSHD myoblasts then fused and developed into myotubes, which produce DUX4. This model approximates natural FSHD biology as much as possible by using primary FSHD-affected muscle cells. The diseases cells are engrafted in one thigh, and healthy human myoblasts in the other thigh, so that each mouse serves as its own control. The compounds also showed repression of DUX4 in these in vivo models, as established by RT-PCR and histological examination.

Example 6—CK1 Inhibitors do not Inhibit Myotube Fusion

Because DUX4 expression increases upon in vitro differentiation of proliferating FSHD myoblasts into multinucleated myotubes (Balog et al., 2015 Epigenetics. 2015; 10(12): 1133-42), inhibition of differentiation might lead to a false positive effect on DUX4 repression.

Bromo- and Extra-Terminal domain (BET) inhibitors such as the non-selective inhibitor (+)JQ1 or the BRD4-selective inhibitor RVX-208 can inhibit the expression of DUX4 in immortalised differentiated myotube cultures (see US2015087636A1). It was shown there that when differentiating myotubes were exposed to (+)JQ1 at the start of the differentiation process, i.e. from the moment when the growth medium was changed to the differentiation medium, the expression of myosin heavy chain (MYH2, a differentiation marker) was decreased, suggesting that the inhibitor also impacted the differentiation process. Both (+)JQ1 and RVX-208 have been evaluated in the phenotypic assay described in this application. Agonists of the beta2 adrenoreceptor have also been reported to inhibit DUX4 expression in differentiating myotubes (Campbell et al., 2017). We evaluated the effect of both BET inhibitors and beta2 adrenoreceptor agonists on the fusion process and compared in to the effect of a CK1 inhibitor.

FIG. 6A shows the experimental setup of Example 2. Compounds are administered either 15 h before fixation, resembling the original screening protocol, or 72 h before fixation (grey arrow). In the latter case, compounds are present during the whole differentiation process. The inventors found that early administration of the BET inhibitor (+)JQ1 (FIG. 6B, C) and agonists of the beta2 adrenoreceptor (FIGS. 6D, E, F, G, H, I) inhibit the fusion process and the differentiation of myoblasts into myotubes. FIG. 6J shows that no myotube formation can be observed after treatment with a beta2 adrenoreceptor agonist (formoterol). This leads to a false positive readout when assessing the DUX4 signal. The BET inhibitor RVX-208 did not show any effect on DUX4 expression, irrespective of treatment time (not shown). While the fusion index did not appear to be affected at the 15 h timepoint, also with this treatment time the myotube fusion process was affected by these compounds as determined by RT-PCR showing inhibition of the expression of the late differentiation marker myosin heavy chain (Myh; not shown; primers were from hMYH2 kit described above).

As illustrated in example 5, inhibition of CK1 inhibits DUX4. This effect occurs without inhibiting myotube fusion, neither after 15 h nor after 72 h of compound treatment (FIG. 6K, L).

Example 7—CK1 Inhibitors Inhibition Profile

Compounds PF-670462, PF-5006739, Compound E, Compound F, Compound D, Compound H, Compound A, and SR3029 were assayed for their inhibition of CK1 α, CK1 δ, CK1 ε, and of p38, and their concurrent repression of DUX4. Table 4 shows inhibitory results.

TABLE 4 inhibition of CK1 and p38 by CK1 inhibitors, in nM

| IC$_{50}$ EC$_{50}$ | PF-670462 | PF-5006739 | E | F | D | H | A | SR-3029 |
|---|---|---|---|---|---|---|---|---|
| CK1 α | 320 | 123 | 592 | 561 | 644 | 33 | 30 | >10k |
| CK1 δ | 29 | 20 | 31 | 18 | 33.1 | 22 | 19 | 346 |
| CK1 ε | 100 | 27 | 84 | 72 | 51.6 | 16 | 12 | 381 |
| p38 | 32 | 74 | 1110 | 677 | 569 | 25 | 13 | >10k |
| DUX4 | 470 | 820 | 1890 | 2590 | 1410 | 10 | 50 | 50 |
|  | (n = 4) | (n = 12) | (n = 4) | (n = 2) | (n = 2) | (n = 2) | (n = 2) |  |

REFERENCES

Balog et al., 2015 Epigenetics. 2015; 10(12):1133-42; Bergerat et al., 2017, DOI: 10.1016/j.prp.2016.11.015; Van den Boogaard et al., 2016, DOI: 10.1016/j.ajhg.2016.03.013; Brockschmidt et al., 2008, DOI: 10.1136/gut.2007.123695; Campbell et al., 2017, DOI: 10.1186/s13395-017-0134-x; Chebib and Jo, 2016, DOI: 10.1002/cncy.21685; Eide E J, Virshup DM, 2001, DOI: 10.1081/CBI-100103963; Etchegaray J P et al., 2009, DOI:10.1128/MCB.00338-09; Geng et al., 2012, DOI: 10.1016/j.devcel.2011.11.013; Kowaljow et al., 2007, DOI: 10.1016/j.nmd.2007.04.002; Lang et al., 2014, DOI: 10.14205/2310-8703.2014.02.01.1; Lemmers et al., 2010, DOI: 10.1126/science.1189044; Lilljebjörn & Fioretos, 2017, DOI: 10.1182/blood-2017-05-742643; Oyama et al., 2017 DOI: 10.1038/s41598-017-04967-0; Paz et al., 2003, DOI: 10.1093/hmg/ddg226; Rickard et al., 2015, DOI: 10.1093/hmg/ddv315; Rudnicki et al., 1993; cell 75(7):1351-9; Sharma et al., 2016, DOI:10.4172/2157-7412.1000303; Snider et al., 2010, DOI: 10.1371/journal.pgen.1001181; Stadler et al., 2013, DOI: 10.1038/nsmb.2571; Tawil et al., 2014, DOI: 10.1186/2044-5040-4-12; Vanderplanck et al., 2011, doi: 10.1371/journal.pone.0026820; Wallace et al., 2011, DOI: 10.1002/ana.22275; Yao et al., 2014, DOI: 10.1093/hmg/ddu251; Yasuda et al., 2016, doi: 10.1038/ng.3535; Young et al., 2013, doi:10.1371/journal.pgen.1003947; Zhang et al., 1999, doi:10.1177/108705719900400206; Zhang et al., 2017, DOI:10.1038/ng.3691 WO2011051858/WO2012085721/WO2015119579/EP2949651/WO2009016286/US2005/0131012/WO2015195880/WO2014081923/US201402213131 US2015087636A1

The invention claimed is:

1. A method of treating facioscapulohumeral muscular dystrophy (FSHD) in a subject in need thereof, the method comprising the step of administering an effective amount of a casein kinase 1 inhibitor to the subject, wherein the casein kinase 1 inhibitor reduces DUX4 expression.

2. The method according to claim 1, wherein the casein kinase 1 inhibitor is administered to a subject 4, 3, 2, or 1 times per day or less, preferably 1 time per day.

3. The method according to claim 1, wherein the casein kinase inhibitor inhibits at least casein kinase 1δ.

4. The method according to claim 1, characterized in that the casein kinase 1 inhibitor is administered to the subject in an amount ranging from 0.1 to 1500 mg/day, preferably from 0.1 to 400 mg/day, more preferably from 0.25 to 150 mg/day.

5. The method according to claim 1, characterized in that the casein kinase 1 inhibitor is administered orally, sublingually, intravascularly, intravenously, subcutaneously, or transdermally, preferably orally.

6. The method according to claim 1, wherein DUX4 expression is reduced by at least 30%, 40%, 60%, 80%, or more.

7. The method according to claim 1, wherein the casein kinase 1 inhibitor reduces DUX4 expression in muscle cells or immune cells.

8. The method according to claim 1, wherein the reduction of DUX4 expression is determined using PCR or immunostaining.

9. The method according to claim 1, wherein the casein kinase 1 inhibitor is from the class comprising an azole core.

10. The method according to claim 1, wherein the casein kinase 1 inhibitor is selected from the group consisting of compounds A, B, C, D, E, F, G, H, I, J, K, L, M, N, O, SR-3029, PF-670462, and PF-5006739;

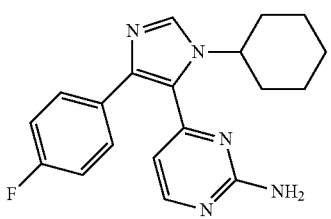

PF-670462

PF-5006739
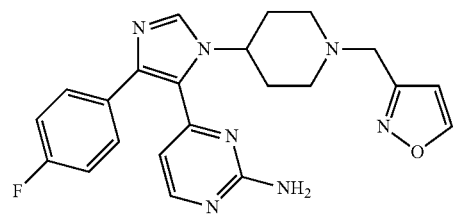
Compound A
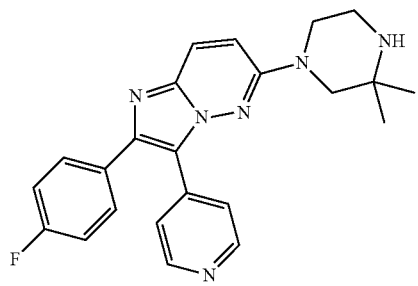
Compound B
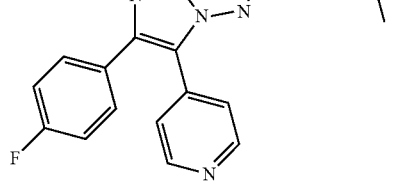
Compound C
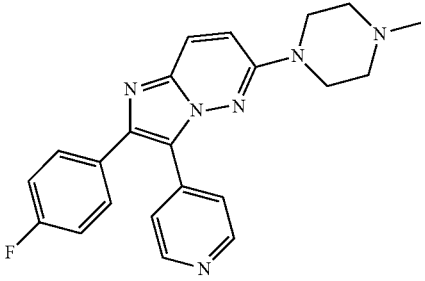
Compound D
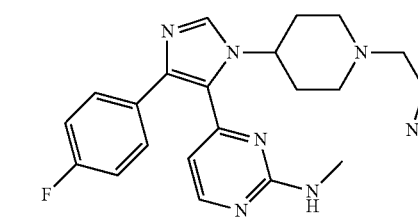
Compound E
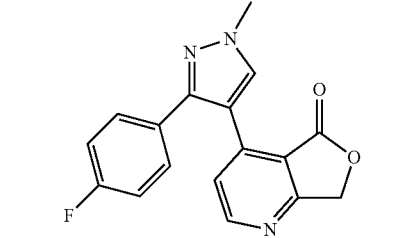
Compound F
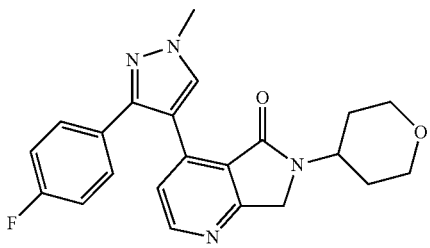
Compound G
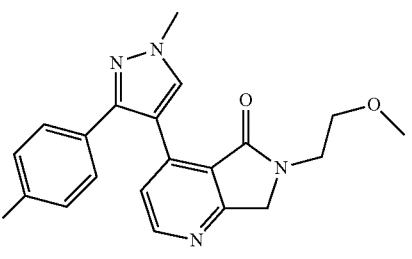
Compound H
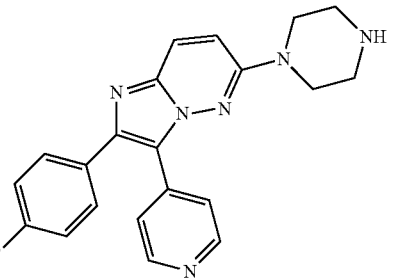
Compound I
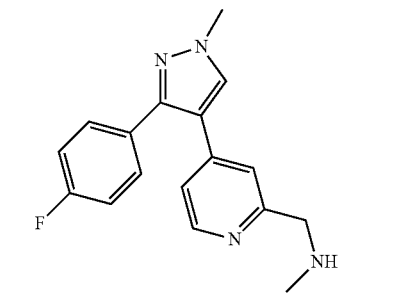
Compound J
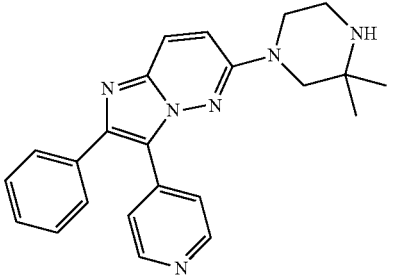

Compound K

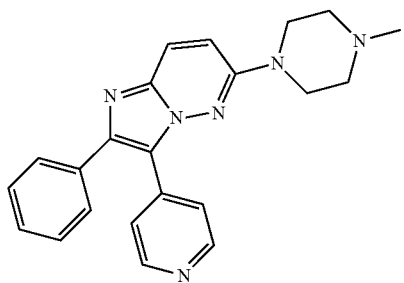

Compound L

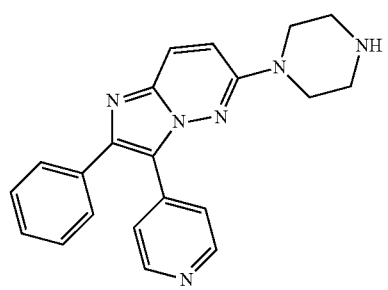

Compound M

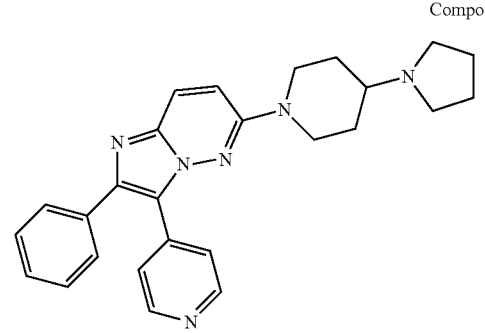

Compound N

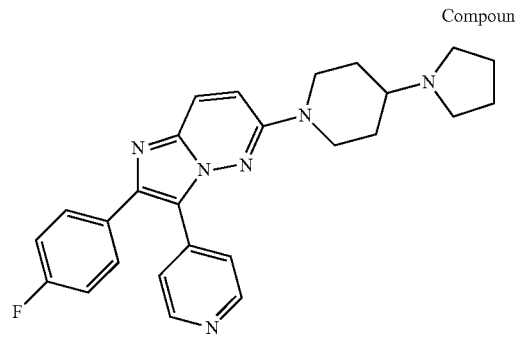

Compound O

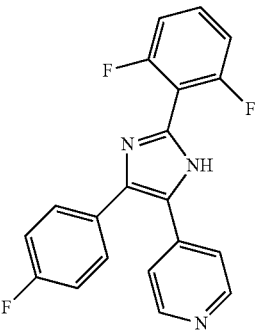

SR-3029

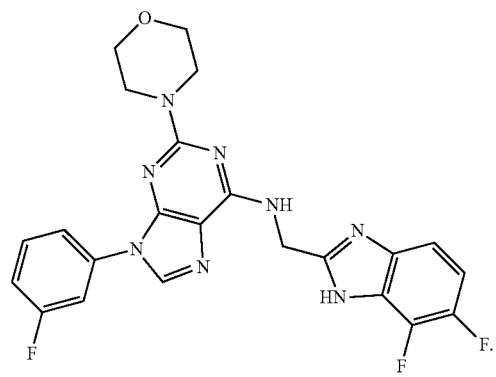

11. The method according to claim 1, wherein the casein kinase 1 inhibitor is in a composition comprising at least one casein kinase 1 inhibitor as defined in claim 1, and a pharmaceutically acceptable excipient.

12. The method according to claim 11, wherein the composition is formulated for oral, sublingual, parenteral, intravascular, intravenous, subcutaneous, or transdermal administration, or for administration by inhalation, preferably for oral administration.

* * * * *